United States Patent
Nakagawa et al.

(10) Patent No.: US 11,684,324 B2
(45) Date of Patent: Jun. 27, 2023

(54) MEDICAL IMAGE DIAGNOSIS APPARATUS AND CONTROLLING METHOD

(71) Applicant: CANON MEDICAL SYSTEMS CORPORATION, Otawara (JP)

(72) Inventors: Shouichi Nakagawa, Otawara (JP); Yohei Matsuzawa, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 43 days.

(21) Appl. No.: 17/305,733

(22) Filed: Jul. 14, 2021

(65) Prior Publication Data
US 2022/0022825 A1    Jan. 27, 2022

(30) Foreign Application Priority Data

Jul. 27, 2020 (JP) .................................. 2020-126390
Jul. 1, 2021 (JP) .................................. 2021-110162

(51) Int. Cl.
*A61B 6/04* (2006.01)
*A61B 6/00* (2006.01)

(52) U.S. Cl.
CPC .......... *A61B 6/0487* (2020.08); *A61B 6/0464* (2013.01); *A61B 6/4447* (2013.01); *A61B 6/469* (2013.01); *A61B 6/488* (2013.01); *A61B 6/5205* (2013.01)

(58) Field of Classification Search
None
See application file for complete search history.

(56) References Cited

U.S. PATENT DOCUMENTS

| | | | |
|---|---|---|---|
| 3,848,132 | A | 11/1974 | Foderaro |
| 7,224,764 | B2 | 5/2007 | Sukovic et al. |
| 2003/0004438 | A1 | 1/2003 | Berthonnaud et al. |
| 2008/0075225 | A1 | 3/2008 | Kalender |
| 2014/0139215 | A1 | 5/2014 | Gregerson et al. |

(Continued)

FOREIGN PATENT DOCUMENTS

| | | | |
|---|---|---|---|
| JP | 2-195945 A | | 8/1990 |
| JP | 8-266650 A | | 10/1996 |

(Continued)

OTHER PUBLICATIONS

Extended European Search Report dated Nov. 23, 2021 in European Patent Application No. 21187475.5, citing documents AA through AG and AO through AR therein, 9 pages.

*Primary Examiner* — Hoon K Song
(74) *Attorney, Agent, or Firm* — Oblon, McClelland, Maier & Neustadt, L.L.P.

(57) ABSTRACT

A medical image diagnosis apparatus according to an embodiment of the present disclosure includes: a gantry, one or more columns, a processing circuitry, and, and a supporting and moving mechanism. The gantry includes an imaging system related to imaging a patient. The one or more columns are each configured to support the gantry so as to be movable in a vertical direction. The processing circuitry generates an image on the basis of an output from the imaging system. The supporting and moving mechanism is configured to support the patient from underneath, while being installed so as to be movable in a direction intersecting the moving direction of the gantry. The processing circuitry controls the moving of the supporting and moving mechanism.

17 Claims, 19 Drawing Sheets

(56) References Cited

U.S. PATENT DOCUMENTS

| | | |
|---|---|---|
| 2015/0117597 A1 | 4/2015 | Jan et al. |
| 2015/0131775 A1 | 5/2015 | Yorkston et al. |
| 2017/0086758 A1 | 3/2017 | McCarthy et al. |
| 2017/0105689 A1 | 4/2017 | Hori |
| 2017/0105691 A1 | 4/2017 | Shindo et al. |
| 2017/0105696 A1 | 4/2017 | Gotanda et al. |
| 2017/0119323 A1 | 5/2017 | Oishi |
| 2018/0055707 A1 | 3/2018 | Stanton |
| 2018/0177473 A1 | 6/2018 | Gregerson et al. |
| 2018/0242937 A1 | 8/2018 | Hasegawa |
| 2018/0353143 A1* | 12/2018 | Gregerson ........... A61B 6/4447 |
| 2019/0059830 A1 | 2/2019 | Williams |
| 2019/0130598 A1 | 5/2019 | Chikamatsu et al. |

FOREIGN PATENT DOCUMENTS

| | | |
|---|---|---|
| JP | 08-322828 A | 12/1996 |
| JP | 2013-128643 A | 7/2013 |
| JP | 2015-198769 A | 11/2015 |
| JP | 2017-080304 A | 5/2017 |
| JP | 2018-050685 A | 4/2018 |
| JP | 2018-050711 A | 4/2018 |
| JP | 2018-110685 A | 7/2018 |
| JP | 2018-121925 A | 8/2018 |
| JP | 2018-130378 A | 8/2018 |
| JP | 2019-536546 A | 12/2019 |

* cited by examiner

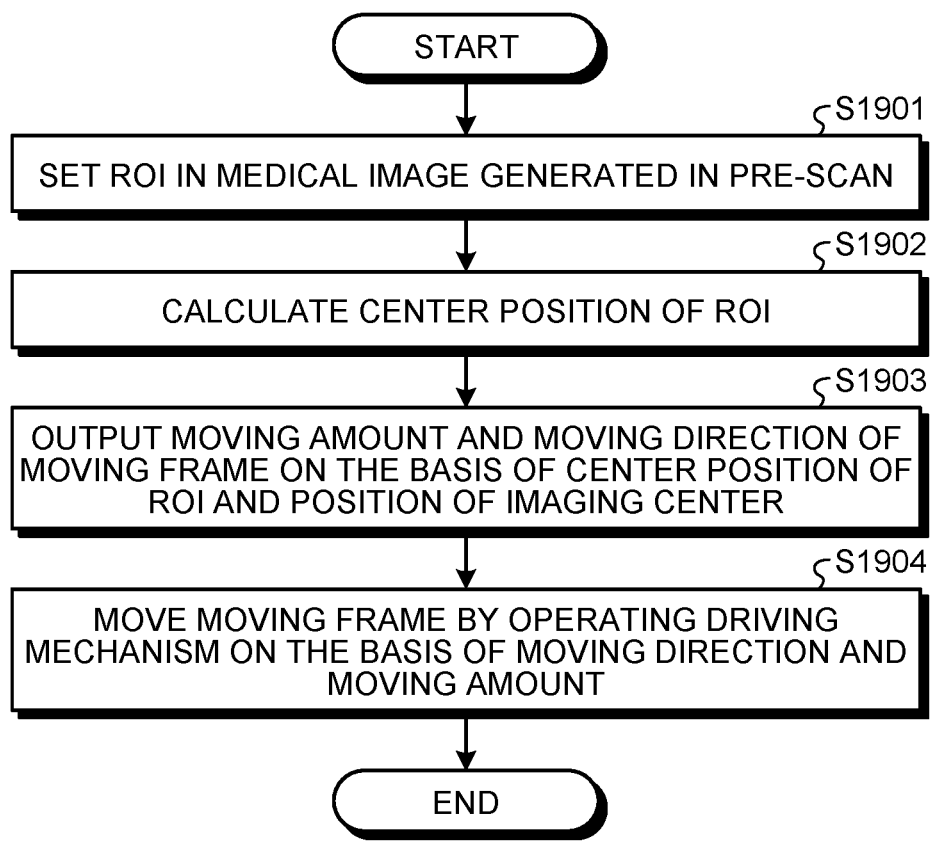

MEDICAL IMAGE DIAGNOSIS APPARATUS AND CONTROLLING METHOD

CROSS-REFERENCE TO RELATED APPLICATIONS

This application is based upon and claims the benefit of priority from Japanese Patent Application No. 2020-126390, filed on Jul. 27, 2020; and Japanese Patent Application No. 2021-110162, filed on Jul. 1, 2021, the entire contents of both of which are incorporated herein by reference.

FIELD

Embodiments described herein relate generally to a medical image diagnosis apparatus and a controlling method.

BACKGROUND

Medical image diagnosis apparatuses that are conventionally known include X-ray Computed Tomography (CT) apparatuses capable of imaging an examined subject (hereinafter, "patient") in a standing state or a sitting state. To prompt the patient to be in a position desired by the user within the imaging space of a medical image diagnosis apparatus, the user gives a verbal instruction to the patient, so that the patient moves according to the instruction from the user. A problem arises where the medical image diagnosis apparatus is unable to obtain medical images with excellent quality, because it is impossible to freely move the patient as intended by the user.

For this reason, medical image diagnosis apparatuses using a mobile terminal may have low throughput of medical examinations.

BRIEF DESCRIPTION OF THE DRAWINGS

FIG. 19 is a flowchart illustrating an example of a procedure in a position aligning process according to the sixth application example of the embodiment.

DETAILED DESCRIPTION

Figure 1:
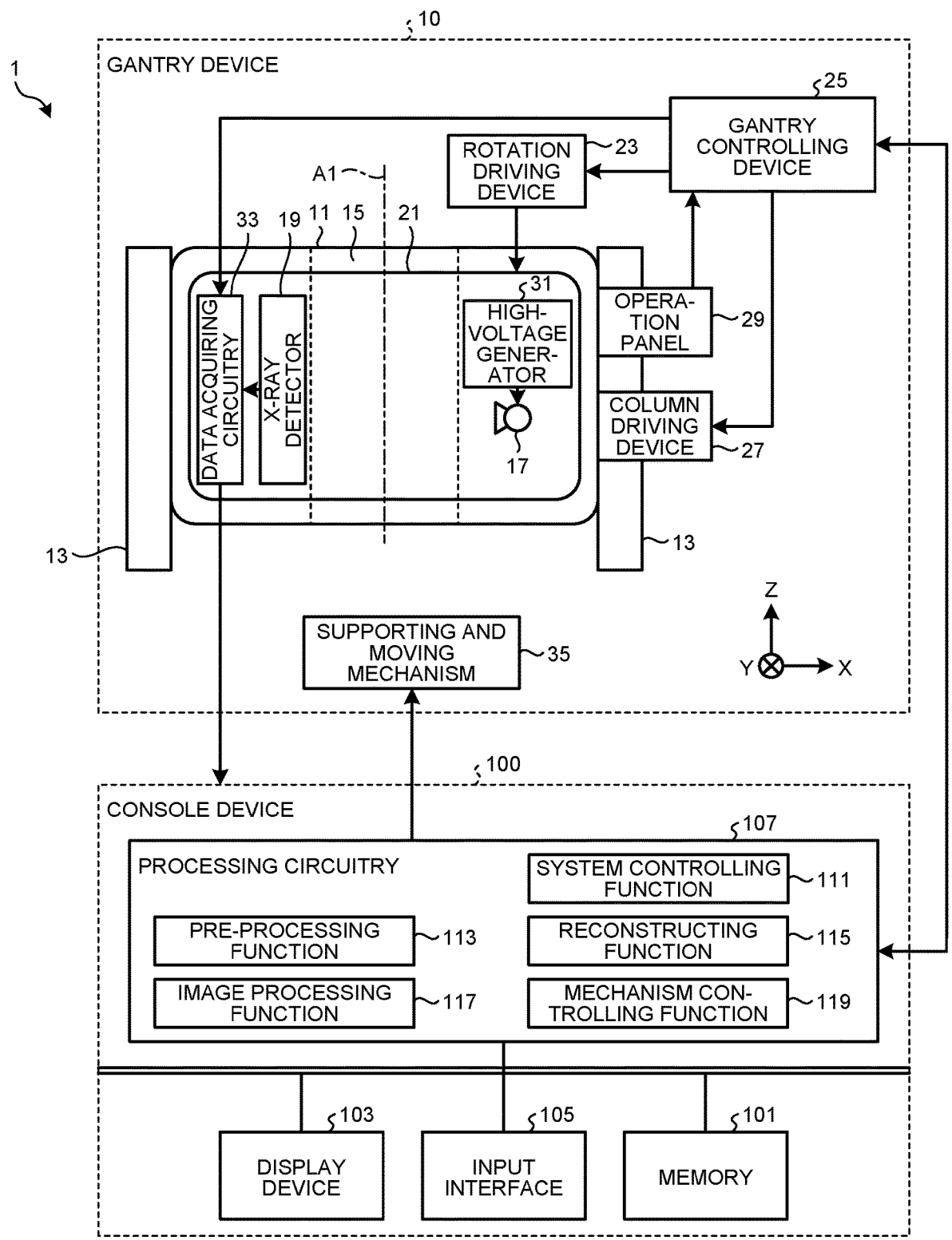
FIG. 1 is a diagram illustrating an exemplary configuration of a standing CT apparatus according to an embodiment.

Exemplary embodiments of a medical image diagnosis apparatus will be explained in detail below, with reference to the accompanying drawings. To explain specific examples, the medical image diagnosis apparatus is assumed to be an X-ray computed tomography apparatus capable of imaging a patient in a standing state or a sitting state (hereinafter, "standing computed tomography [CT] apparatus"). The standing state denotes a state in which the patient is standing on the floor surface on which a standing CT apparatus 1 is installed. The sitting state denotes a state in which the patient is sitting on a wheelchair or a chair (hereinafter, "wheelchair or the like"). It is sufficient when the standing CT apparatus 1 is capable of imaging a patient at least in the standing state.

The medical image diagnosis apparatus according to the exemplary embodiments are not limited to the standing CT apparatus 1. For example, it is possible to realize, as appropriate, technical concepts of the present embodiments with a magnetic resonance imaging apparatus or a nuclear medicine diagnosis apparatus capable of imaging a patient in a standing state or a sitting state. In the embodiments described below, some of the constituent elements having mutually the same reference characters are assumed to perform mutually the same operations, and duplicate explanations thereof will be omitted as appropriate.

Embodiments

A medical image diagnosis apparatus according to an embodiment of the present disclosure includes: a gantry, one or more columns, a processing circuitry, and a supporting and moving mechanism. The gantry includes an imaging system related to imaging a patient. The one or more columns are each configured to support the gantry so as to be movable in a vertical direction. The processing circuitry generates an image on the basis of an output from the imaging system. The supporting and moving mechanism is configured to support the patient from underneath, while being installed so as to be movable in a direction intersecting the moving direction of the gantry. The processing circuitry controls the moving of the supporting and moving mechanism.

FIG. 1 is a diagram illustrating an exemplary configuration of the standing CT apparatus 1 according to an embodiment of the present disclosure. As illustrated in FIG. 1, the standing CT apparatus 1 according to the present embodiment includes a gantry device 10 and a console device 100. For example, the gantry device 10 is installed in a CT imaging room, whereas the console device 100 is installed in a control room adjacent to a CT examination room. The gantry device 10 and the console device 100 are connected in a wired or wireless manner so as to be able to communicate with each other. In the present embodiment, the axial direction (the vertical direction) perpendicular to the floor surface is defined as a Z-axis direction, whereas the two directions orthogonal to the Z-axis direction and orthogonal to each other are defined as an X-axis direction and a Y-axis direction.

The gantry device 10 is a scan device having a configuration for performing an X-ray CT imaging process on a patient in a sitting state or a standing state. The console device 100 is a computer configured to control the gantry device 10. The gantry device 10 includes a gantry 11, columns 13, a rotation driving device 23, a gantry controlling circuitry 25, a column driving device 27, an operation panel 29, and a supporting and moving mechanism 35.

The gantry 11 has an opening 15 forming an imaging space related to the imaging of the patient. For example, the gantry 11 is a structure that has a substantially circular cylindrical shape and in which the opening 15 is formed. As illustrated in FIG. 1, the gantry 11 houses therein an X-ray tube 17 and an X-ray detector 19 arranged so as to oppose each other while the opening 15 is interposed therebetween. The X-ray tube 17 and the X-ray detector 19 are included in an imaging system related to the imaging of the patient according to the present embodiment. The imaging system may further include a data acquiring circuitry (hereinafter, "Data Acquisition System [DAS]") 33, a high-voltage generator 31, a collimator, a wedge, and/or the like. In other words, the gantry 11 includes the imaging system related to the imaging of the patient. The gantry 11 is supported by the columns 13 so as to be movable in the vertical directions along the columns 13.

The gantry 11 includes: a main frame (not illustrated) formed by using metal such as aluminum; and a rotating frame 21 supported by the main frame so as to be rotatable on a rotation axis A1 via a bearing or the like. An annular electrode (not illustrated) is provided in a contact part between the main frame and the rotating frame 21. To the contact part of the main frame, an electrically-conductive slider (not illustrated) is attached so as to be slidably in contact with the annular electrode.

The columns 13 are base bodies configured to support the gantry 11 apart from the floor surface. For example, the columns 13 each have a columnar shape such as a circular cylindrical shape or a prismatic shape. For example, the columns 13 are formed by using an arbitrary material such as plastic and/or metal. For example, the columns 13 are attached to lateral face parts of the gantry 11. The columns 13 are configured to support the gantry 11 so as to be slidable perpendicularly to the floor surface, while the gantry 11 is oriented so that the rotation axis A1 of the opening 15 is substantially perpendicular to the floor surface for the purpose of performing the X-ray CT imaging process on the patient in a sitting or standing posture.

Typically, the columns 13 are provided in two lateral parts of the gantry 11; however, the present embodiment is not limited to this example. For instance, a single column 13 may be connected to only one of the two lateral parts of the gantry 11. In other words, at least one column 13 is configured to support the gantry 11 so as to be movable in the vertical directions. Further, although the columns 13 are described to each have a columnar shape, the present embodiment is not limited to this example. For instance, the one or more columns 13 may have any shape such as a U-shape, as long as it is possible to support at least one of the lateral parts of the gantry 11.

In this situation, the columns 13 do not necessarily have to fix the gantry 11 in such a manner that the rotation axis A1 is perpendicular to the floor surface. In other words, the columns 13 may be configured to support the gantry 11 so as to be rotatable on a horizontal axis (hereinafter, "tilt axis") extending parallel to the floor surface. In that situation, it is desirable to connect the columns 13 and the gantry 11 in such a manner that the gantry 11 is rotatable on the tilt axis via a bearing or the like.

The X-ray tube 17 is a vacuum tube configured to generate X-rays by causing thermo electrons to be emitted from a negative pole (a filament) toward a positive pole (a target), with application of high voltage and a supply of a filament current from the high-voltage generator 31. As a result of the thermo electrons colliding with the target, the X-rays are generated. The X-rays generated at an X-ray tube focal point of the X-ray tube 17 are, for example, formed to have a cone beam shape via a collimator and are radiated onto a patient P. For instance, examples of the X-ray tube 17 include a rotating anode X-ray tube configured to generate the X-rays by having the thermo electrons emitted onto a rotating anode. The present embodiment is applicable to both a standing CT apparatus including a single X-ray tube and a so-called multi-X-ray-tube standing CT apparatus in which a plurality of pairs each made up of the X-ray tube 17 and the X-ray detector 19 are installed on the rotating frame 21.

The X-ray detector 19 is configured to detect X-rays that were radiated from the X-ray tube 17 and have passed through the patient P and is configured to output an electrical signal corresponding to the amount of the X-rays to the DAS 33. For example, the X-ray detector 19 includes a plurality of rows of detecting elements in each of which a plurality of detecting elements are arranged in a channel direction along an arc while being centered on the focal point of the X-ray tube 17. For example, the X-ray detector 19 has a structure in which the plurality of rows of detecting elements are arranged in a slice direction (a row direction). Possible examples of the standing CT apparatus 1 include a Rotate/Rotate type (a third generation CT) in which the X-ray tube 17 and the X-ray detector 19 integrally rotate around the patient P and a Stationary/Rotate type (a fourth generation CT) in which a large number of X-ray detecting elements arrayed in a ring form are fixed, while only the X-ray tube 17 is configured to rotate around the patient P. The present embodiment is applicable to both of these types. In the following sections, to explain specific examples, the standing CT apparatus 1 of the present embodiment is assumed to be a third generation CT apparatus.

Further, for example, the X-ray detector 19 is an indirect-conversion type detector including a grid, a scintillator array, and an optical sensor array. The scintillator array includes a plurality of scintillators each of which includes a scintillator crystal that outputs light in a photon quantity corresponding to the amount of incident X-rays. The grid is arranged on a surface of the scintillator array that is positioned on the X-ray incident side and includes an X-ray blocking plate having a function of absorbing scattered X-rays. The grid may be referred to as a collimator (a one-dimensional collimator or a two-dimensional collimator) in some situations. The optical sensor array has a function of converting the light amounts from the scintillators into corresponding electrical signals and includes optical sensors configured with Photomultiplier Tubes (PMTs), for example. Alternatively, the X-ray detector 19 may be a detector of a direct conversion type that includes a semiconductor element configured to convert X-rays becoming incident thereto into an electrical signal. In another example, the X-ray detector 19 may be an X-ray detector of a photon counting type. The X-ray detector 19 is an example of an X-ray detecting unit.

The rotating frame 21 has the opening 15 and has attached thereto the X-ray tube 17 configured to generate the X-rays. More specifically, the rotating frame 21 is an annular frame configured to support the X-ray tube 17 and the X-ray detector 19 so as to oppose each other and configured to rotate the X-ray tube 17 and the X-ray detector 19 via the gantry controlling circuitry 25 (explained later). The rotating frame 21 is rotatably supported on the main frame via a support bearing. The rotating frame 21 is configured to rotate on the rotation axis A1 with a constant angular speed, by receiving motive power from the rotation driving device 23 that is under control of the gantry controlling circuitry 25.

In addition to the X-ray tube 17 and the X-ray detector 19, the rotating frame 21 further includes and supports the high-voltage generator 31 and the DAS 33. The rotating frame 21 configured in this manner is housed in a casing having a substantially circular cylindrical shape in which the opening 15 serving as the imaging space is formed. The central axis of the opening 15 matches the rotation axis A1 of the rotating frame 21. Further, detection data generated by the DAS 33 is, for example, transmitted from a transmitter including a light emitting diode (LED), to a receiver including a photodiode and being provided in a non-rotation part (e.g., the main frame) of the gantry device 10, through optical communication, and is further transferred to the console device 100. The method for transmitting the detection data from the rotating frame 21 to the non-rotation part of the gantry device 10 is not limited to the optical communication described above and may be realized with any of other contactless data transfer methods.

The rotation driving device 23 is configured to generate the motive power to rotate the rotating frame 21 according to the control exercised by the gantry controlling circuitry 25. The rotation driving device 23 generates the motive power by realizing the driving at a rotation speed corresponding to a duty cycle or the like of a drive signal from the gantry controlling circuitry 25. For example, the rotation driving device 23 is realized by using a motor such as a direct drive motor or a servo motor. For example, the rotation driving device 23 is housed in the gantry 11.

According to commands from the console device 100, the gantry controlling circuitry 25 is configured to control the high-voltage generator 31, the rotation driving device 23, the column driving device 27, and the DAS 33. The gantry controlling circuitry 25 has a function of receiving input signals from an input interface attached to the console device 100 or to the gantry device 10 and controlling operations of the gantry device 10. For example, by receiving the input signals, the gantry controlling circuitry 25 exercises control to rotate the rotating frame 21 and control to tilt the gantry device 10. The gantry controlling circuitry 25 may be provided for the gantry device 10 or may be provided for the console device 100.

As hardware resources, the gantry controlling circuitry 25 includes: a processing device (a processor) such as a Central Processing Unit (CPU) or a Micro Processing Unit (MPU); and a storage device (a memory) such as a Read-Only Memory (ROM) and/or a Random Access Memory (RAM). Further, the gantry controlling circuitry 25 may be realized by using an Application Specific Integrated Circuit (ASIC), a Field Programmable Gate Array (FPGA), or any of other types of Complex Programmable Logic Devices (CPLDs) and Simple Programmable Logic Devices (SPLDs).

The processing device is configured to realize the above-mentioned function by reading and executing a program saved in the storage device. Instead of saving the program in the storage device, it is also acceptable to directly incorporate the program in the circuit of the processing device. In that situation, the processing device realizes the abovementioned function by reading and executing the program incorporated in the circuit thereof.

A driving device (hereinafter, "column driving device") 27 to slide the gantry 11 in the perpendicular directions is housed in at least one of the columns 13 as illustrated in FIG. 1. The column driving device 27 is configured to generate motive power to slide the gantry 11 in the perpendicular directions, according to control exercised by the gantry controlling circuitry 25. More specifically, the column driving device 27 generates the motive power by realizing the driving at the rotation speed corresponding to a duty cycle of the like of a drive signal from the gantry controlling circuitry 25. By receiving the motive power from the column driving device 27, the columns 13 slides the gantry 11 in the perpendicular directions with respect to the columns 13. The column driving device 27 may be realized by using a motor such as a servo motor, for example.

The operation panel 29 is realized by using a switch button, a touchpad on which input operations can be performed by touching an operation surface thereof, a touch panel display device in which a display screen and a touchpad are integrally formed, and/or the like. The operation panel 29 is configured to convert input operations received from the user into electrical signals and to output the electrical signals to the gantry controlling circuitry 25. For example, the operation panel 29 is configured to receive a selecting operation to select from between: a sitting imaging mode in which the patient is imaged while in a sitting posture; and a standing imaging mode in which the patient is imaged while in a standing posture.

The high-voltage generator 31 includes electrical circuits such as a transformer, a rectifier, and the like and is configured to generate the high voltage to be applied to the X-ray tube 17 and the filament current to be supplied to the X-ray tube 17. Further, the high-voltage generator 31 is configured to control the output voltage in accordance with the X-rays radiated by the X-ray tube 17. The high-voltage generator 31 may be of a transformer type or of an inverter type. Further, the high-voltage generator 31 may be provided on the rotating frame 21 or may be provided so as to belong to the main frame of the gantry device 10.

The wedge (not illustrated) is a filter for adjusting the X-ray amount of the X-rays radiated from the X-ray tube 17. More specifically, the wedge is a filter configured to pass and attenuate the X-rays radiated from the X-ray tube 17, so that the X-rays radiated from the X-ray tube 17 onto the patient P have a predetermined distribution. For example, the wedge may be a wedge filter or a bow-tie filter and is a filter obtained by processing aluminum so as to have a predetermined target angle and a predetermined thickness.

The collimator (not illustrated) is configured with lead plates or the like used for narrowing down the X-rays having passed through the wedge into an X-ray radiation range and is configured to form a slit with a combination of the plurality of lead plates or the like.

The DAS 33 includes an amplifier configured to perform an amplifying process on the electrical signals output from the X-ray detecting elements of the X-ray detector 19; and an Analog/Digital (A/D) converter configured to convert electrical signals into digital signals. The DAS 33 is configured to generate the detection data. The detection data generated by the DAS 33 is transferred to the console device 100.

The supporting and moving mechanism 35 is installed so as to be movable in the directions (the X-axis direction and the Y-axis direction) intersecting the vertical direction (the Z direction), which are the moving direction of the gantry 11. The supporting and moving mechanism 35 is configured to support the patient from underneath, i.e., upward in the vertical direction. For example, the supporting and moving mechanism 35 is installed on the floor surface underneath the opening 15 of the gantry 11. More specifically, the supporting and moving mechanism 35 includes: a tabletop configured to support the patient; and a moving mechanism configured to move the tabletop in one or both of the X-axis direction and the Y-axis direction (i.e., the horizontal directions). The tabletop corresponds to a footing for the patient. When the patient is in a standing state underneath the opening 15, the tabletop representing the top face of the supporting and moving mechanism 35 supports the soles of the patient. Further, the tabletop is provided with a sole guide that guides positional arrangements of the soles of the patient. The sole guide is provided in the vicinity of the center of gravity of the tabletop, i.e., in a central part of the tabletop.

For example, the moving mechanism includes: at least one guide (e.g., a linear guide such as a linear motion guide) having a block that supports the tabletop and a rail that guides the block; and a driving mechanism configured to move the block of the guide along the rail. The driving mechanism includes, for example, any of various types of motors to generate a driving force and any of various types of transmission mechanisms (e.g., a ball screw, a chain, or a belt) to transmit the driving force to the block. According to a control signal output from a mechanism controlling function 119 (explained later), the supporting and moving mechanism 35 is configured to generate the driving force by employing the driving mechanism. By using the generated driving force, the supporting and moving mechanism 35 is configured to move the tabletop along the horizontal direction. The supporting and moving mechanism 35 may have a structure capable of supporting the patient in a sitting state. For example, a chair or the like may be installed with on tabletop or the block.

The console device 100 includes a memory 101, a display device 103, an input interface 105, and a processing circuitry 107. Data communication among the memory 101, the display device 103, the input interface 105, and the processing circuitry 107 may be carried out via a bus, for example.

The memory 101 is a storage device configured to store therein various types of information, such as a Hard Disk Drive (HDD), a Solid State Drive (SSD), or an integrated circuit storage device. For example, the memory 101 stores therein projection data and reconstructed image data. Instead of the HDD or the SSD, the memory 101 may be a driving device configured to read and write various types of information from and to a portable storage medium such as a Compact Disc (CD), a Digital Versatile Disc (DVD), or a flash memory, or a semiconductor memory element such as a Random Access Memory (RAM). Further, a saving region of the memory 101 may be provided within the standing CT apparatus 1 or within an external storage device connected via a network. Further, the memory 101 is configured to store therein a control program according to the present embodiment. The memory 101 is configured to store therein volume data or the like generated in a pre-scan and a main scan. Further, the memory 101 is configured to store therein the center position (hereinafter, "imaging center") of the opening 15 for the imaging, in correspondence with the position of the gantry 11 with respect to the columns 13.

The display device 103 is configured to display various types of information. For example, the display device 103 outputs, among others, a medical image (a CT image) generated by the processing circuitry 107 and a Graphical User Interface (GUI) used for receiving various types of operations from the user. For example, as the display device 103, it is possible to use, as appropriate, a Liquid Crystal Display (LCD) device, a Cathode Ray Tube (CRT) display device, an Organic Electroluminescence Display (OELD) device, a plasma display device, or any other arbitrary display device. Further, the display device 103 may be provided on the gantry device 10. Further, the display device 103 may be of a desktop type or may be configured by using a tablet terminal or the like capable of wirelessly communicating with the main body of the console device 100. The display device 103 corresponds to a display unit.

The input interface 105 is configured to receive various types of input operations from the user, to convert the received input operations into electrical signals, and to output the electrical signals to the processing circuitry 107. For example, the input interface 105 receives, from the user, an acquisition condition used at the time of acquiring the projection data, a reconstruction condition used at the time of reconstructing a CT image, an image processing condition used at the time of generating a post-processing image from a CT image, and the like. As the input interface 105, for example, it is possible to use, as appropriate, a mouse, a keyboard, a trackball, a switch, a button, a joystick, a touchpad, a touch panel display device, and/or the like.

In the present embodiment, the input interface 105 does not necessarily have to include one or more physical operation component parts such as the mouse, the keyboard, the trackball, the switch, the button, the joystick, the touchpad, the touch panel display device, and/or the like. For instance, possible examples of the input interface 105 include an electrical signal processing circuit configured to receive an electrical signal corresponding to an input operation from an external input device provided separately from the device and to output the electrical signal to a processing circuitry 107. Further, the input interface 105 is an example of an input unit. In another example, an input interface 105 may be provided for the gantry device 10. Furthermore, the input interface 105 may be configured by using a tablet terminal or the like capable of wirelessly communicating with the main body of a console device 100. The input interface 105 corresponds to an input unit.

The processing circuitry 107 is configured to control operations of the entirety of the standing CT apparatus 1 in accordance with the electrical signals representing the input operations and being output from the input interface 105. For example, as hardware resources, the processing circuitry 107 includes a processor such as a CPU, an MPU, or a Graphics Processing Unit (GPU) and a memory such as a ROM and/or a RAM. By employing the processor configured to execute programs loaded into the memory, the processing circuitry 107 is configured to execute a system controlling function 111, a pre-processing function 113, a reconstructing function 115, an image processing function 117, and the mechanism controlling function 119. The processing circuitry 107 configured to execute the system controlling function 111, the pre-processing function 113, the reconstructing function 115, the image processing function 117, and the mechanism controlling function 119 correspond to a system controlling unit, a pre-processing unit, an image generating unit, an image processing unit, and a mechanism controlling unit. In this situation, the system controlling function 111, the pre-processing function 113, the reconstructing function 115, the image processing function 117, and the mechanism controlling function 119 do not each necessarily have to be realized by using a single processing circuit. It is also acceptable to structure a processing circuit by combining together a plurality of independent processors so that the system controlling function 111, the pre-processing function 113, the reconstructing function 115, the image processing function 117, and the mechanism controlling function 119 are realized as a result of the processors executing the programs.

By employing the system controlling function 111, the processing circuitry 107 is configured to control the functions of the processing circuitry 107 on the basis of the input operations received from the user via the input interface 105. More specifically, the system controlling function 111 is configured to read the control program stored in the memory 101, to load the read control program into a memory in the processing circuitry 107, and to control functional units of the standing CT apparatus 1 according to the loaded control program. For example, on the basis of the input operations received from the user via the input interface 105, the processing circuitry 107 is configured to control the functions of the processing circuitry 107.

By employing the pre-processing function 113, the processing circuitry 107 is configured to generate data obtained by performing pre-processing processes such as a logarithmic conversion process, an offset correcting process, an inter-channel sensitivity correcting process, a beam hardening correction, and/or the like on the detection data output from the DAS 33. The data before the pre-processing processes will be referred to as raw data, whereas the data after the pre-processing processes will be referred to as projection data.

By employing the reconstructing function 115, the processing circuitry 107 is configured to generate CT image data by performing a reconstructing process that uses a Filtered Back Projection (FBP) method, a successive approximation reconstruction method, or the like, on the projection data generated by the pre-processing function 113. In other words, the reconstructing function 115 is configured to generate an image on the basis of the output from the imaging system. The reconstructing function 115 is configured to store data of the reconstructed CT image into the memory 101.

By employing the image processing function 117, the processing circuitry 107 is configured to perform various types of image processing processes on the CT image reconstructed by the reconstructing function 115. For example, the image processing function 117 generates a display image by performing, on the CT image, three-dimensional image processing processes such as volume rendering, surface volume rendering, an image value projecting process, a Multi-Planar Reconstruction (MPR) process, and/or a Curved MPR (CPR) process. Further, when a Region Of Interest (hereinafter, "ROI") is input, via the input interface 105, in a medical image (hereinafter, "pre-scan image") generated in the pre-scan, the image processing function 117 is configured to calculate the center position of the ROI.

By employing the mechanism controlling function 119, the processing circuitry 107 is configured to control moving of the supporting and moving mechanism 35. For example, on the basis of the ROI in the pre-scan image and the imaging center of the imaging system, the mechanism controlling function 119 controls the moving of the supporting and moving mechanism 35. More specifically, the mechanism controlling function 119 controls the moving of the supporting and moving mechanism 35 so as to align the center position of the ROI with the position of the imaging center. In this situation, the position in the ROI to be aligned with the position of the imaging center does not necessarily have to be the center position and may be the center of gravity of the ROI, for example.

More specifically, on the basis of the center position of the ROI and the position of the imaging center, the mechanism controlling function 119 is configured to output information (hereinafter, "recommended moving amount") corresponding to one or both of a moving direction and a moving amount of the supporting and moving mechanism 35. The recommended moving amount corresponds to a control value related to controlling the moving of the supporting and moving mechanism 35. In this situation, on the basis of the output information, i.e., according to the control value represented by the recommended moving amount, the mechanism controlling function 119 controls the moving of the supporting and moving mechanism 35. The mechanism controlling function 119 configured to output the recommended moving amount corresponds to an output unit.

Further, the mechanism controlling function 119 may output, to the display device 103, the information corresponding to one or both of the moving direction and the moving amount of the supporting and moving mechanism 35. In that situation, when the user inputs an operation related to the moving of the supporting and moving mechanism 35 on the basis of the displayed information, the mechanism controlling function 119 controls the moving of the supporting and moving mechanism 35 according to the input operation. Further, the mechanism controlling function 119 may control the moving of the supporting and moving mechanism 35 according to an instruction from the user based on the ROI in the pre-scan image and the imaging center of the imaging system. Further, the mechanism controlling function 119 may control the moving of the supporting and moving mechanism 35 according to an instruction from the user to align the center position of the ROI with the position of the imaging center.

Figure 2:
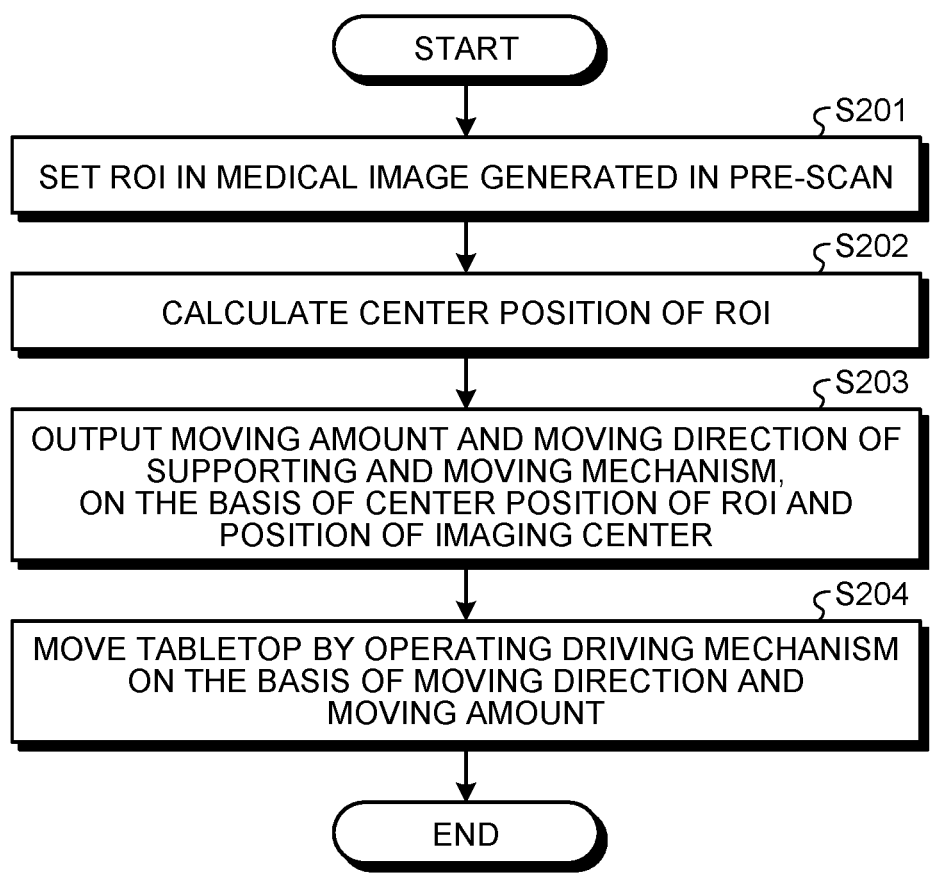
FIG. 2 is a flowchart illustrating an example of a procedure in a position aligning process according to the embodiment.
Figure 3:
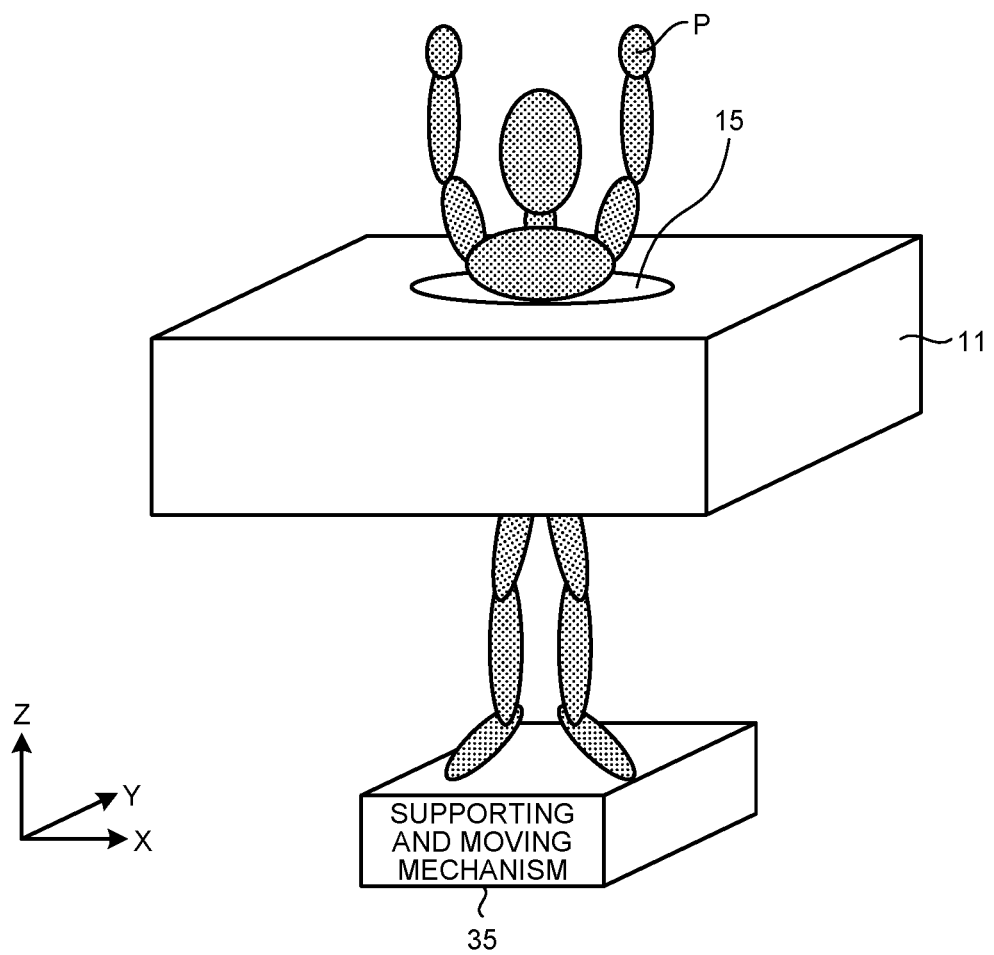
FIG. 3 is a drawing according to the embodiment illustrating an example at the time of performing a pre-scan on a patient positioned in a standing state on a supporting and moving mechanism.

The position aligning process performed by the standing CT apparatus 1 according to the present embodiment configured as described above will be explained, with reference to FIG. 2. The position aligning process denotes controlling the moving of the supporting and moving mechanism 35, so as to align the center position of the ROI with the imaging center. FIG. 2 is a flowchart illustrating an example of a procedure in the position aligning process according to the embodiment. The position aligning process Step S201:

A ROI is set in the pre-scan image generated in the pre-scan. More specifically, the patient is placed in a standing state on the supporting and moving mechanism 35 installed underneath the opening 15. Subsequently, under the control of the system controlling function 111, the imaging system performs the pre-scan on the patient. FIG. 3 is a drawing illustrating an example at the time of performing the pre-scan on the patient P positioned in a standing state on the supporting and moving mechanism 35. As illustrated in FIG. 3, the pre-scan is performed on the patient P contained in the imaging space at the opening 15.

By employing the pre-processing function 113, the processing circuitry 107 generates projection data related to the pre-scan. Subsequently, by employing the reconstructing function 115, the processing circuitry 107 generates volume data by performing a reconstructing process while using the generated projection data. By employing the image processing function 117, the processing circuitry 107 generates the pre-scan image by performing the MPR process on the volume data. The display device 103 displays the pre-scan image. The input interface 105 sets the ROI in the pre-scan image according to an instruction from the user.

Figure 4:
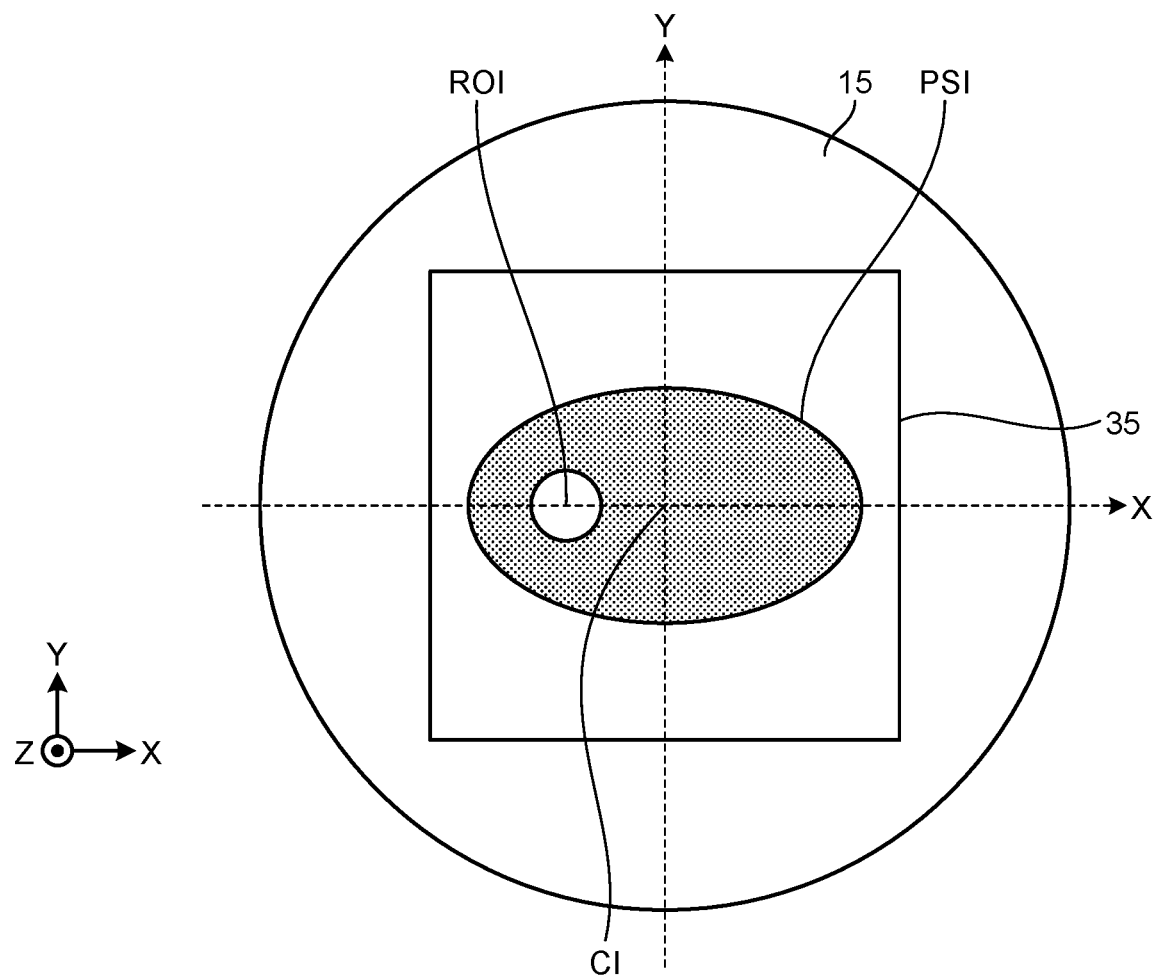
FIG. 4 is a drawing according to the embodiment illustrating an example of a positional relationship among a region of interest being set in a pre-scan image, an opening, and the supporting and moving mechanism being.

FIG. 4 is a drawing illustrating an example of a positional relationship among the ROI being set in a pre-scan image PSI, the opening 15, and the supporting and moving mechanism 35. As illustrated in FIG. 4, an imaging center CI which yields excellent image quality may be different from the center of the ROI.

Step S202:

By employing the image processing function 117, the processing circuitry 107 calculates the center position of the ROI within the displayed image. When the ROI has a circular shape, the center position corresponds to the center of the circle. In another example, when the ROI has an oval shape, the center position corresponds to the middle point of the major axis or the minor axis of the oval, for example. In yet another example, when the ROI has a polygonal shape, the center position corresponds to the center of gravity of the ROI. At this time, the processing circuitry 107 may cause a monitor provided on the gantry 11 or at least one of the columns 13 or the display device 103 to display the ROI, the center position of the ROI, and the position of the imaging center, so as to be superimposed on the pre-scan image PSI. In this situation, via the input interface 105, the user may input a moving direction and a moving amount of the supporting and moving mechanism 35 by using a vector indicated with an arrow, or the like, for example.

Step S203:

By employing the mechanism controlling function 119, the processing circuitry 107 outputs a recommended moving amount on the basis of the center position of the ROI and the position of the imaging center. Further, the mechanism controlling function 119 may cause a monitor provided on the gantry 11 or at least one of the columns 13 or the display device 103 to display the recommended moving amount, together with the center position of the ROI and the position of the imaging center. With this arrangement, it is possible to inform the user of the recommended moving amount. The recommended moving amount corresponds to, for example: the direction (the moving direction) from the center position of the ROI toward the position of the imaging center; and the distance between the center position of the ROI and the position of the imaging center. In other words, the recommended moving amount corresponds to a vector amount from the center position of the ROI toward the position of the imaging center. Further, the mechanism controlling function 119 may cause the display device 103 to display the recommended moving amount, together with the pre-scan image. In that situation, the user may revise, as appropriate, the recommended moving amount, via the input interface 105.

Figure 5:
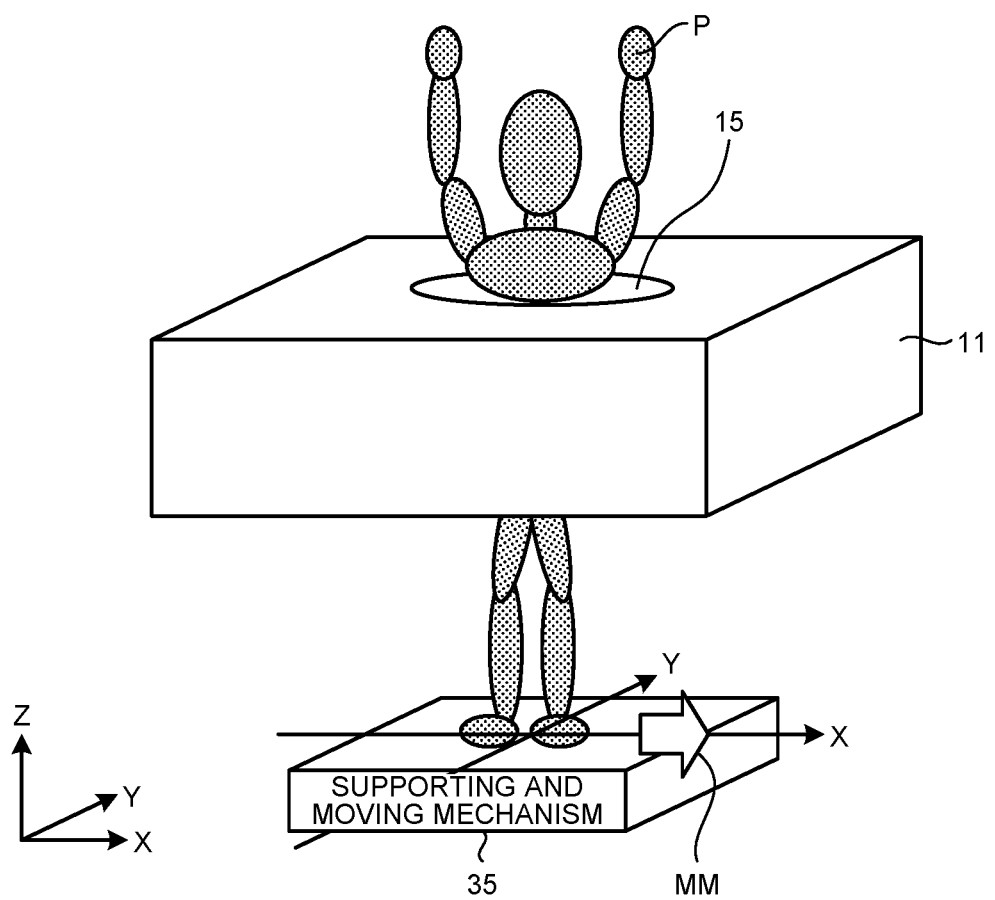
FIG. 5 is a drawing according to the embodiment illustrating an example of a manner in which a mechanism controlling function moves the supporting and moving mechanism with respect to the pre-scan image illustrated in FIG. 4.

Step S204:

By employing the mechanism controlling function 119, the processing circuitry 107 moves the tabletop by operating the driving mechanism on the basis of the moving direction and the moving amount. In this situation, the mechanism controlling function 119 may manually move the supporting and moving mechanism 35 in accordance with a moving amount input or revised by the user or the recommended moving amount, according to an instruction from the operator provided via the input interface 105. FIG. 5 is a drawing illustrating an example of a manner in which the mechanism controlling function 119 moves the supporting and moving mechanism 35 with respect to the pre-scan image PSI illustrated in FIG. 4. As illustrated in FIG. 4, the center position of the ROI is positioned on the left-hand side of the imaging center CI on the X-axis. For this reason, as illustrated in FIG. 5, the mechanism controlling function 119 moves the supporting and moving mechanism 35 by a moving amount MM being output, in the "+" direction along the X-axis.

Figure 6:
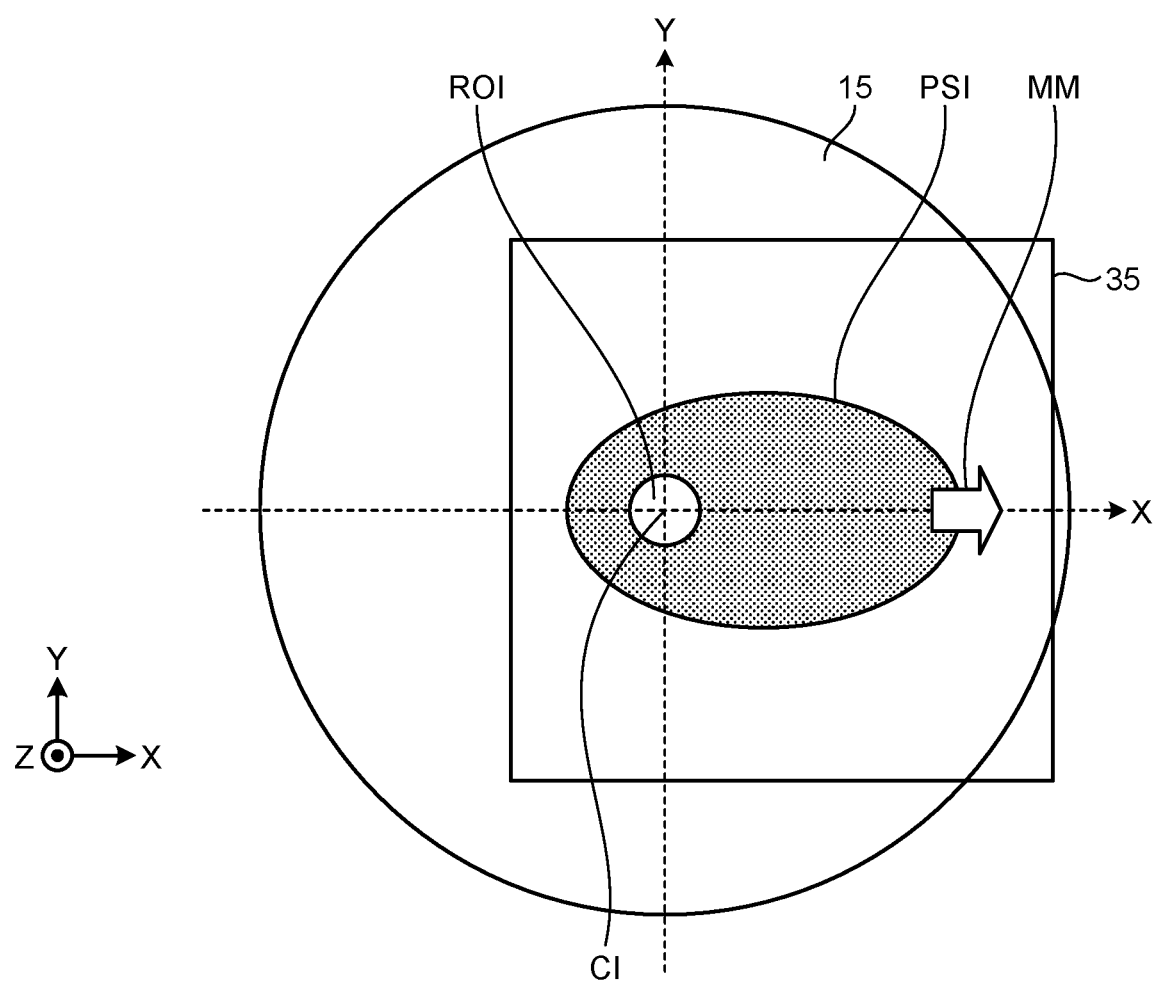
FIG. 6 is a drawing according to the embodiment illustrating an example after the supporting and moving mechanism in FIG. 5 is moved, together with the pre-scan image, the region of interest, and an imaging center.

FIG. 6 is a drawing illustrating an example after the supporting and moving mechanism 35 in FIG. 5 is moved, together with the pre-scan image PSI, the ROI, and the imaging center. As illustrated in FIG. 6, after the supporting and moving mechanism 35 is moved by the moving amount MM, the center position of the ROI is aligned with the position of the imaging center. As a result, the center position of the ROI substantially coincides with the position of the imaging center, which makes it possible to obtain a medical image having excellent quality in a main scan to be performed after the present step in the position aligning process.

The standing CT apparatus 1 according to the embodiment described above includes: the gantry 11 that includes the imaging system related to the imaging of the patient P; the one or more columns 13 configured to support the gantry 11 so as to be movable in the vertical directions; the image generating unit configured to generate the pre-scan image PSI on the basis of the output from the imaging system; the supporting and moving mechanism 35 configured to support the patient P from underneath, while being installed so as to be movable in the directions intersecting the moving directions of the gantry 11; and the mechanism controlling unit configured to control the moving of the supporting and moving mechanism 35. With this configuration, by using the standing CT apparatus 1 described herein, it is possible to control the moving of the supporting and moving mechanism 35 so that, on the basis of the region of interest within the pre-scan image PSI and the imaging center of the imaging system, the center position of the region of interest is aligned with the position of the imaging center, for example.

Further, when the standing CT apparatus 1 according to the present embodiment is used, the information corresponding to one or both of the moving direction and the moving amount of the supporting and moving mechanism 35 is output on the basis of the region of interest of the patient P and the imaging center of the imaging system, so as to control the moving of the supporting and moving mechanism 35 on the basis of the output information. Further, when the standing CT apparatus 1 according to the embodiment is used, it is possible to control the moving of the supporting and moving mechanism 35, according to an instruction from the user based on the region of interest within the pre-scan image PSI and the imaging center of the imaging system, e.g., according to an instruction from the user to align the center position of the region of interest with the position of the imaging center. For example, the output information is displayed on the display device 103, so that when the user inputs, via the input interface 105, an operation related to the moving of the supporting and moving mechanism 35, on the basis of the displayed information, it is possible to control the moving of the supporting and moving mechanism 35 according to the input operation.

Consequently, by using the standing CT apparatus 1 according to the embodiment, it is possible to cause the center position of the ROI set within the pre-scan image PSI to be aligned with the imaging center either automatically or according to the instruction from the user. In other words, the user is able to arrange the ROI at the imaging center as intended, without the need to give a verbal instruction or the like to the patient P. As a result, by using the standing CT apparatus 1, it is possible to generate a medical image having excellent quality from the main scan performed on the patient P. Furthermore, when the standing CT apparatus 1 described herein is used, because it is possible to arrange the ROI at the imaging center without the need to give a verbal instruction or the like to the patient P, it is possible to improve throughput of the medical examination of the patient P.

A Modification Example

Figure 7:
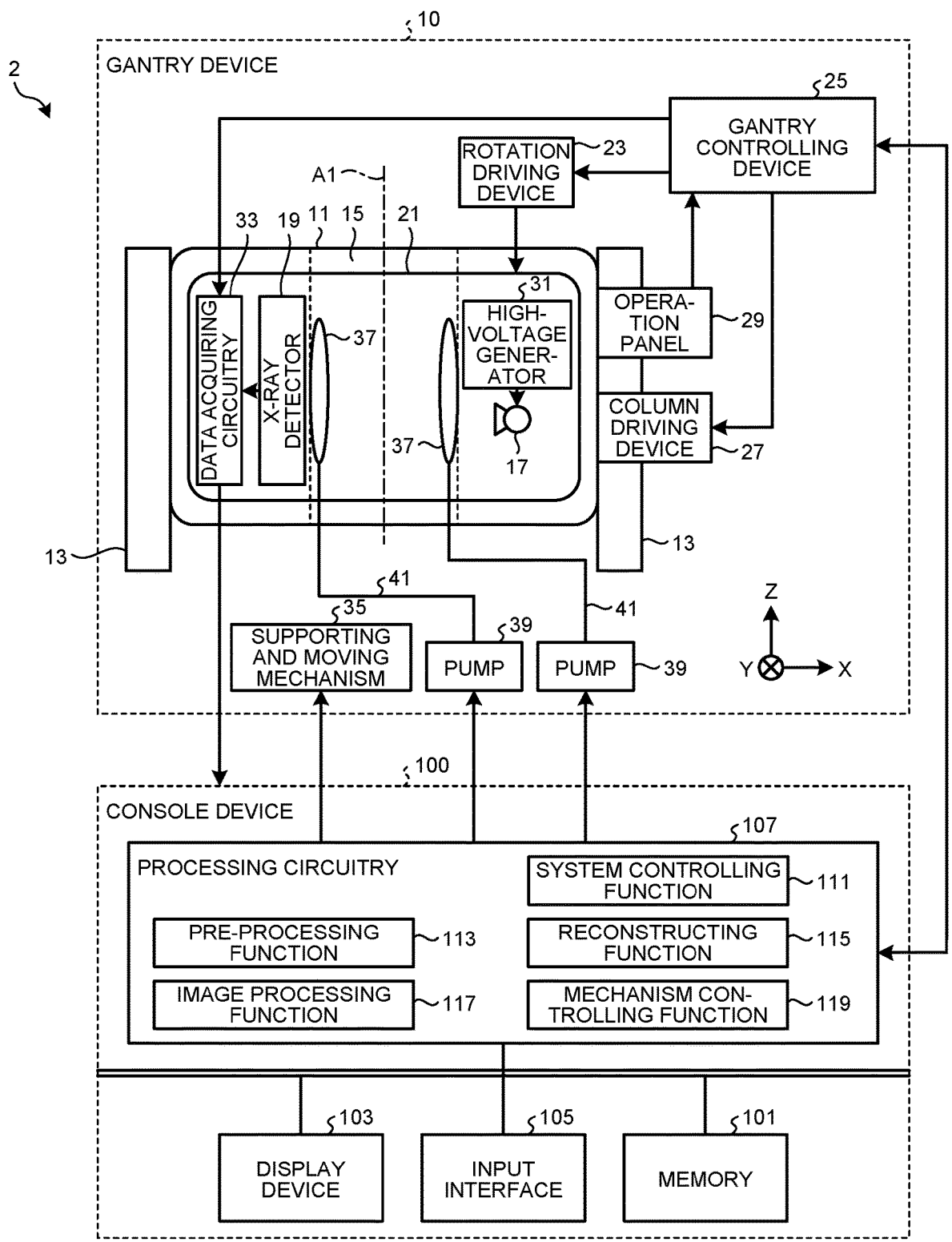
FIG. 7 is a drawing illustrating an exemplary configuration of a standing CT apparatus according to a modification example of the embodiment.

In a modification example described herein, a plurality of gas bags that can be inflated with injection of gas and are capable of keeping (stabilizing) the patient P are provided on a lateral face of the opening 15, so that the injection of the gas into the gas bags and ejection of the gas from the gas bags are controlled in conjunction with the control over the moving of the supporting and moving mechanism 35. FIG. 7 is a drawing illustrating an exemplary configuration of a standing CT apparatus 2 according to the present modification example. The standing CT apparatus 2 illustrated in FIG. 7 further includes a plurality of gas bags 37 and a plurality of pumps 39, in addition to the standing CT apparatus 1 illustrated in FIG. 1. Alternatively, the technical features of the present modification example may be carried out alone without being accompanied by the control over the moving of the supporting and moving mechanism 35. In other words, the supporting and moving mechanism 35 may be omitted when the present modification example is carried out.

The plurality of gas bags 37 are provided on a wall surface of the gantry 11 at the opening 15. For example, the plurality of gas bags 37 are inflatable with the injection of the gas and deflatable with the ejection of the gas and are structured by using a material that does not attenuate radiation such as X-rays. The plurality of gas bags 37 are inflated by the injection of the gas and are configured to maintain the posture of the patient P. Via hoses 41, the plurality of gas bags 37 are connected to the plurality of pumps 39. The gas may be air, for example. In that situation, the gas bags 37 may be referred to as airbags. However, the gas does not necessarily have to be air and may be a gas different from air. The plurality of gas bags 37 may be removable from the gantry 11. Further, the plurality of gas bags 37 may be provided with a cover or a drape that is removable and configured to cover the plurality of gas bags 37. The cover or drape is structured by using a material that does not attenuate radiation such as X-rays. Further, each of the plurality of gas bags 37 may be provided with a pressure sensor configured to detect the pressure of the gas filling the gas bag 37.

Figure 8:
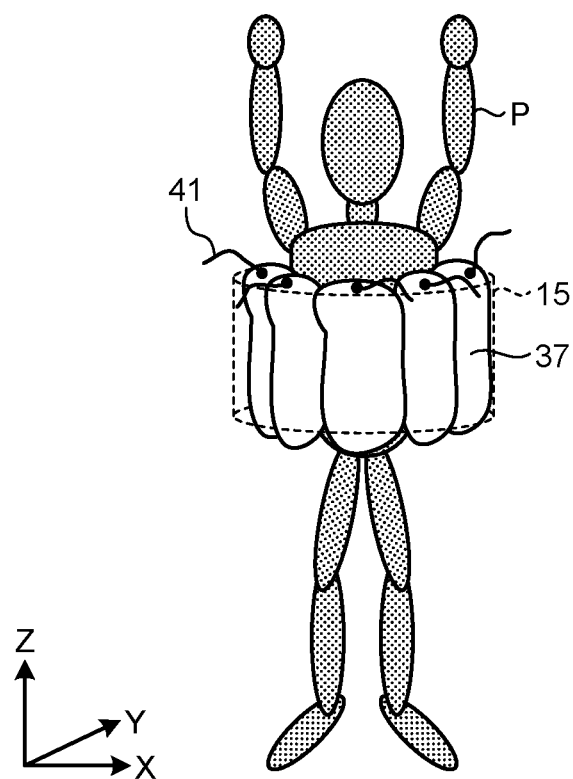
FIG. 8 is a drawing according to the modification example of the embodiment illustrating an example of a positional relationship of a plurality of gas bags with respect to the patient.

FIG. 8 is a drawing illustrating an example of a positional relationship of the plurality of gas bags 37 with respect to the patient P. The gantry 11 is not illustrated in FIG. 8. As illustrated in FIG. 8, each of the plurality of gas bags 37 is provided with the hose 41 used for injecting the gas and ejecting the gas. Further, as illustrated in FIG. 8, the gas bags 37 filled with the gas are arranged around the patient P at the opening 15. In other words, because the gas bags 37 being filled with the gas and having a predetermined level of pressure are positioned between the wall surface of the gantry 11 and the patient P at the opening 15, the posture of the patient P is maintained.

As illustrated in FIG. 8, each of the plurality of gas bags 37 is in close contact with the gas bags positioned adjacent thereto. Although FIG. 7 illustrates only the plurality of gas bags 37 and two of the plurality of pumps 39, in actuality two or more gas bags are provided on the wall surface of the gantry 11 at the opening 15, as illustrated in FIG. 8. In addition, the plurality of pumps 39 are provided on the gantry device 10 or the like in accordance with the quantity of the gas bags 37. Alternatively, in place of the plurality of gas bags 37, one gas bag partitioned to have a plurality of sections may be used. In that situation, the plurality of pumps 39 are connected to the plurality of sections via the plurality of hoses 41, while each pump is kept in correspondence with a different one of the plurality of sections.

Under the control of the mechanism controlling function 119, the plurality of pumps 39 are configured to inject the gas into the plurality of gas bags 37 and to eject the gas from the plurality of gas bags 37. It is possible to install the plurality of pumps 39 and the hoses 41 in arbitrary locations that are outside the imaging space, in such a position that causes no interference with the rotation of the rotating frame 21, the moving of the gantry 11, or the moving of the supporting and moving mechanism 35.

Figure 9:
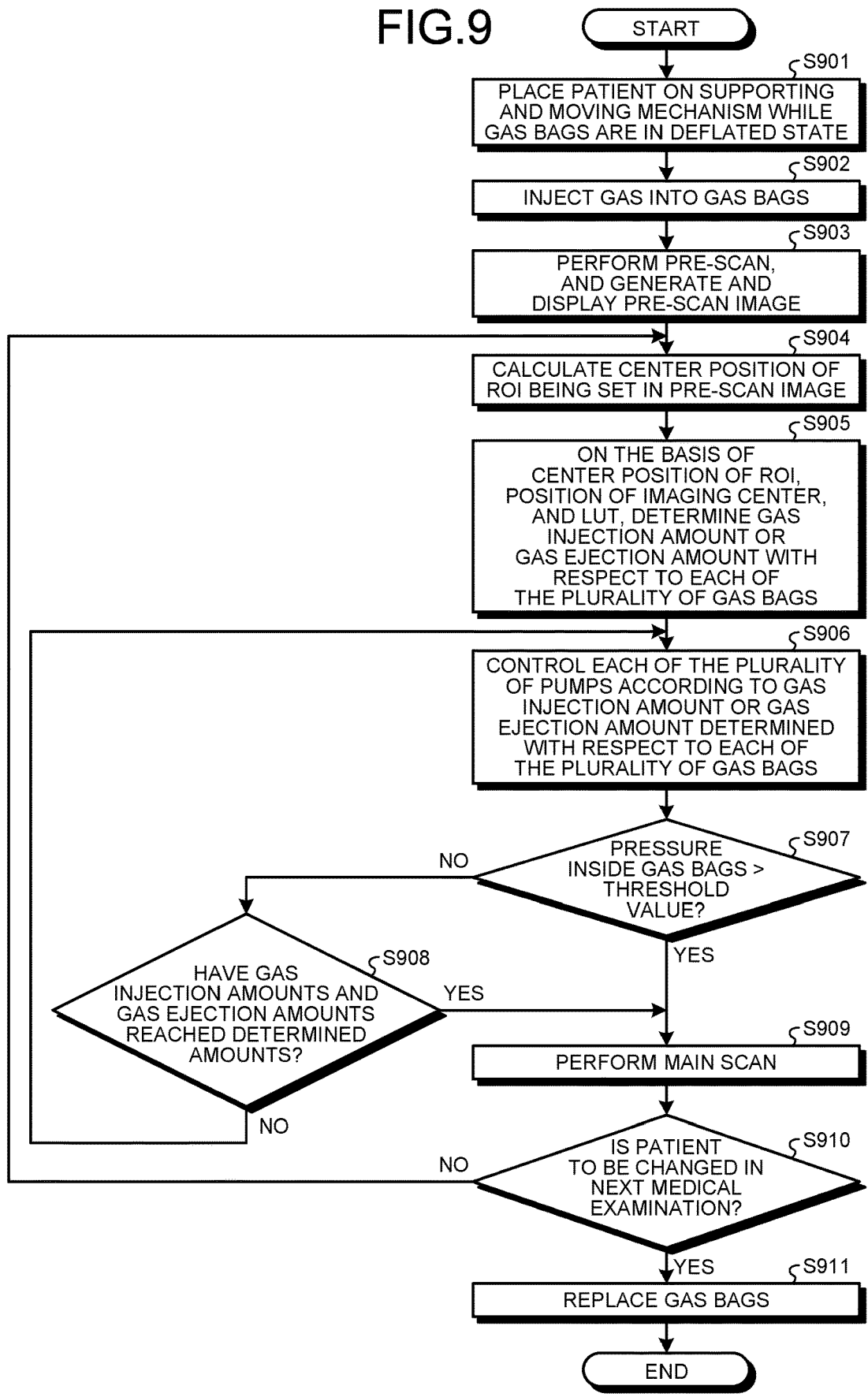
FIG. 9 is a flowchart illustrating an example of a procedure in a pump controlling process according to the modification example of the embodiment.

By employing the mechanism controlling function 119, the processing circuitry 107 is configured to further control the injection of the gas and the ejection of the gas by the plurality of pumps 39, in conjunction with the control over the moving of the supporting and moving mechanism 35. While the gas is injected into any one of the gas bags 37, when the pressure inside the gas bag 37 (hereinafter, "bag internal pressure") has reached a predetermined threshold value (hereinafter, "pressure threshold value"), the mechanism controlling function 119 controls the pump 39 connected to the gas bag 37 so as to stop the injection of the gas. A process (hereinafter, "pump controlling process") related to controlling the plurality of pumps 39 in relation to the injection of the gas and the ejection of the gas will be explained, with reference to FIG. 9. FIG. 9 is a flowchart illustrating an example of a procedure in the pump controlling process.

The Pump Controlling Process

Step S901:

Before a pre-scan is performed, while the plurality of gas bags 37 are in a deflated state, the patient P is placed on the supporting and moving mechanism 35. In the situation where the gas bags 37 are filled with gas before the patient P is placed on the supporting and moving mechanism 35, the mechanism controlling function 119 controls the pumps 39 so as to eject the gas from the gas bags 37. In that situation, under the control of the mechanism controlling function 119, the pumps 39 eject the gas from the gas bags 37. After that, the patient P is placed on the supporting and moving mechanism 35.

Step S902:

As a result of the mechanism controlling function 119 controlling the pumps 39, gas is injected into the gas bags 37. The amount of the gas to be injected into the gas bags 37 (hereinafter, "gas injection amount") is determined by the mechanism controlling function 119, for example, on the basis of the weight and the height in patient information of the patient P related to the medical examination. In this situation, the mechanism controlling function 119 controls the pumps 39 until the determined injection amount is reached. Alternatively, the mechanism controlling function 119 may control the pumps 39 until the bag internal pressure levels detected by the pressure sensors provided for the gas bags 37 reach the pressure threshold value. The pressure threshold value is stored in the memory 101 in advance.

Step S903:

The imaging system performs a pre-scan on the patient P, under the control of the system controlling function 111. By employing the pre-processing function 113, the processing circuitry 107 generates projection data related to the pre-scan. By employing the reconstructing function 115, the processing circuitry 107 generates volume data by performing a reconstructing process while using the generated projection data. By employing the image processing function 117, the processing circuitry 107 generates a pre-scan image PSI by performing the MPR process on the volume data. The display device 103 displays the pre-scan image PSI.

Step S904:

The input interface 105 sets an ROI in the pre-scan image PSI according to an instruction from the user. By employing the image processing function 117, the processing circuitry 107 calculates the center position of the ROI in the displayed image.

Step S905:

By employing the mechanism controlling function 119, the processing circuitry 107 determines a gas injection amount or an amount of gas to be ejected (hereinafter, "gas ejection amount") with respect to each of the plurality of gas bags 37, on the basis of a correspondence table indicating center positions of the ROI and positions of the imaging center. For example, the correspondence table is a correspondence table (hereinafter, "ROI movement correspondence table") indicating, for each of the plurality of gas bags 37, a correspondence relationship between gas injection amounts and gas ejection amounts, with respect to differences between the center position of the ROI and the position of the imaging center, directions from the center position of the ROI toward the position of the imaging center, and weights and heights of the patient P. The ROI movement correspondence table is stored in the memory 101 in advance.

Figure 10:
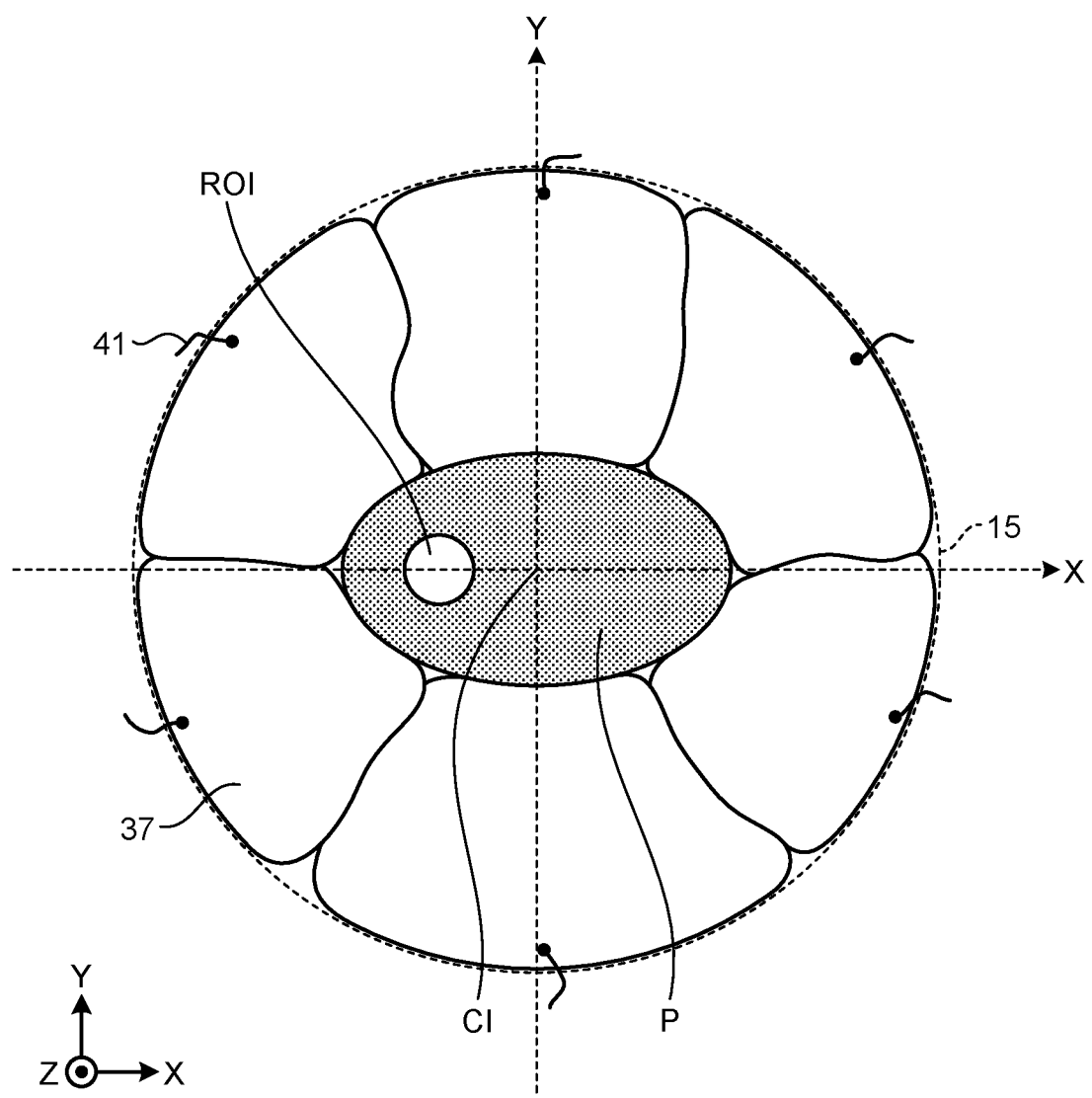
FIG. 10 is a drawing according to the modification example of the embodiment illustrating an example of a positional relationship among the region of interest of the patient, the opening, and a plurality of gas bags at the time of a pre-scan.

FIG. 10 is a drawing illustrating an example of a positional relationship among the ROI of the patient P, the opening 15, and the plurality of gas bags 37 at the time of a pre-scan. As illustrated in FIG. 10, an imaging center CI that yields excellent image quality is different from the center of the ROI. In the present step, for example, gas injection amounts and gas ejection amounts to align the center of the ROI with the imaging center are determined as illustrated in FIG. 10. With respect to each of the plurality of gas bags 37, the processing circuitry 107 may cause the display device 103 or a monitor provided on the gantry 11 to display a gas injection amount or a gas ejection amount. In that situation, the mechanism controlling function 119 is capable of manually revising the gas injection amounts and the gas ejection amounts, according to an instruction from the operator provided via the input interface 105.

Figure 11:
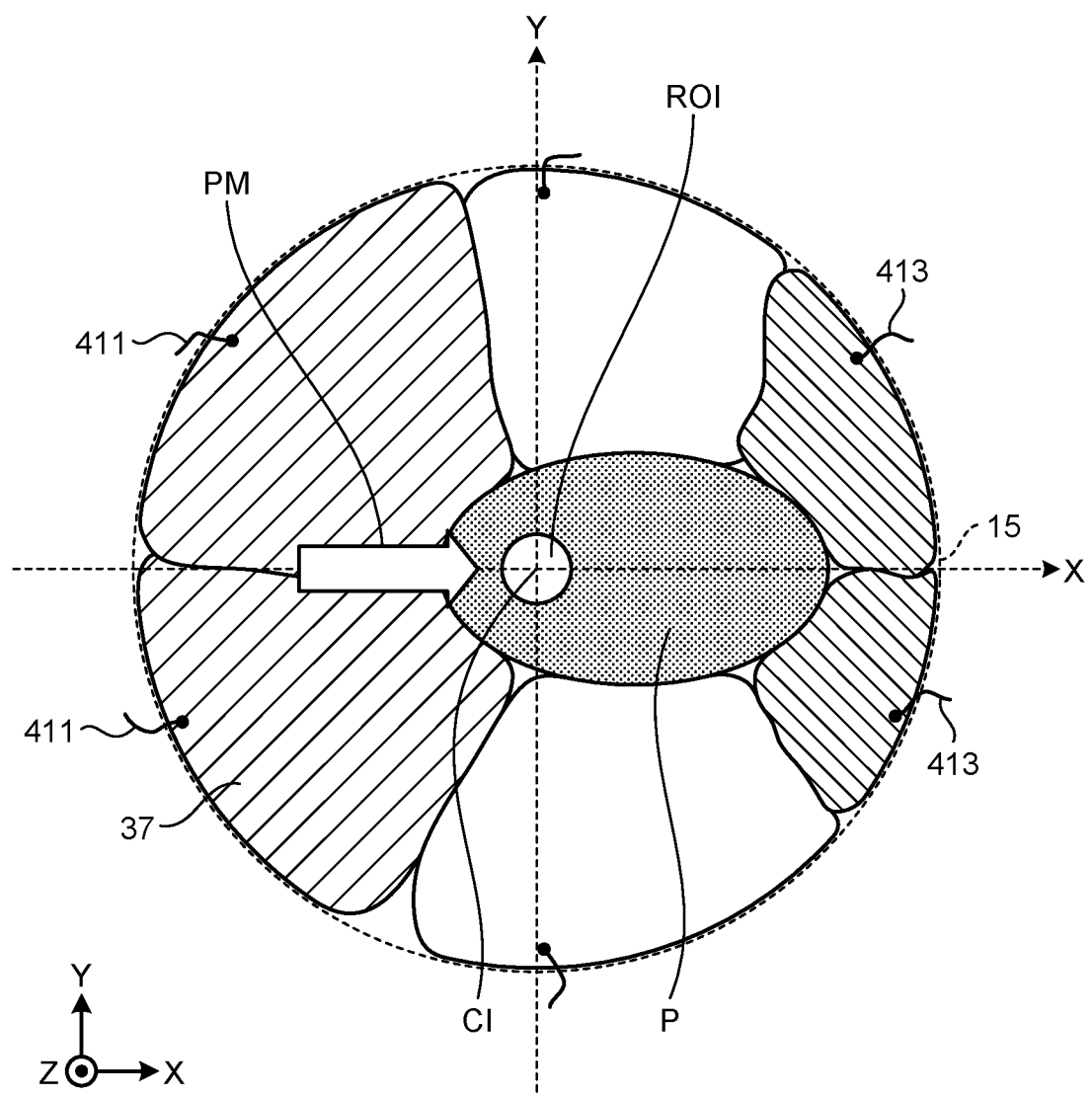
FIG. 11 is a drawing according to the modification example of the embodiment illustrating an example in relation to FIG. 10 regarding injecting gas into each of the plurality of gas bags and ejecting gas from each of the plurality of gas bags.

Step S906:

By employing the mechanism controlling function 119, the processing circuitry 107 controls each of the plurality of pumps 39 according to the gas injection amount or the gas ejection amount determined with respect to each of the plurality of gas bags 37. FIG. 11 is a drawing illustrating an example in relation to FIG. 10 regarding injecting the gas into each of the plurality of gas bags 37 and ejecting the gas from each of the plurality of gas bags 37. As illustrated in FIG. 11, gas is injected via two hoses 411 into the two gas bags positioned on the left-hand side of the ROI, whereas gas is ejected via two hoses 413 from the two gas bags positioned on the right-hand side of the ROI. As a result, the patient P is moved along a direction PM, as illustrated in FIG. 11. When the process at the present step is performed, the process at step S204 is also performed at the same time. In other words, in conjunction with the control over the moving of the supporting and moving mechanism 35, the mechanism controlling function 119 further controls the injection of the gas and the ejection of the gas by the pumps 39. In this situation, the mechanism controlling function 119 may manually control the pumps 39, according to an instruction from the operator provided via the input interface 105.

Step S907:

When the pressure in at least one of the plurality of gas bags 37 exceeds the threshold value (step S907: Yes), the process at step S909 will be performed. On the contrary, when the pressure in none of the plurality of gas bags 37 has exceeded the threshold value (step S907: No), the process at step S908 will be performed.

Step S908:

When the gas injection amounts and the gas ejection amounts of the plurality of gas bags 37 reach the amounts determined at step S905 (step S908: Yes), the process at step S909 will be performed. On the contrary, when the gas injection amounts and the gas ejection amounts of the plurality of gas bags 37 have not reached the amounts determined at step S905 (step S908: No), the process at step S906 will be performed.

Step S909:

According to an instruction from the user provided via the input interface 105, a main scan is performed on the patient P under the control of the system controlling function 111. In this situation, the processing circuitry 107 generates projection data by employing the pre-processing function 113. Subsequently, by employing the reconstructing function 115, the processing circuitry 107 reconstructs volume data on the basis of the projection data. After that, by employing the image processing function 117, the processing circuitry 107 generates a medical image (hereinafter, "main scan image") related to the main scan, on the basis of the volume data.

Step S910:

In the next medical examination, if the patient P is not to be changed (step S910: No), i.e., when another medical examination is to be performed on the same patient, the processes at step S904 and thereafter will be repeatedly performed. In this situation, when the ROI is unchanged in the further examination of the patient P, the process at step S909 may be performed. On the contrary, when the patient P is to be a different patient in the next examination (step S910: Yes), the process at step S911 will be performed.

Step S911:

The user replaces the gas bags 37. Alternatively, instead of replacing the gas bags 37, the user may disinfect the gas bags 37. Further, when the gas bags 37 are provided with a cover or a drape, the user replaces the cover or drape. In the time period between the affirmative judgment result (Yes) at step S910 and the end of the present step, a monitor provided on the gantry 11 or at least one of the columns 13 or the display device 103 may display a character string or information suggesting that the gas bags 37 and the cover or drape be replaced or that the gas bags 37 be disinfected. With this arrangement, it is possible to prompt the user to replace the gas bags 37 and the cover or drape or to disinfect the gas bags 37 and the like. Further, in this situation, the character string or the information, i.e., the information suggesting that the gas bags 37 and the cover or drape be replaced or that the gas bags 37 be disinfected and the like, may be brought into a non-display state according to an instruction from the user provided via the input interface 105, for example. Further, the present process at step S911 (i.e., the replacement of the gas bags 37 and the cover or drape or the disinfection of the gas bags 37) may be performed once a day, e.g., when all the medical examinations of the day have been finished.

When the standing CT apparatus 2 according to the modification example described above is used, the injection of the gas and the ejection of the gas by the pumps 39 are further controlled, in conjunction with the control over the moving of the supporting and moving mechanism 35, in relation to the injection of the gas into and the ejection of the gas from each of the plurality of gas bags 37 provided on the wall surface of the gantry 11 at the opening 15. With this arrangement, it is possible to automatically cause the center position of the ROI set within the pre-scan image PSI to be aligned with the imaging center, while the posture of the patient P is maintained, i.e., fixed. Consequently, it is possible to enhance the precision level of the positional alignment of the ROI with the imaging center and to enhance stability at the time of moving the patient P. Further, by using the standing CT apparatus 2 described herein, it is possible to prevent the situation where the CT image from the main scan becomes blurry due to the upper body of the patient P being unstable. Consequently, by using the standing CT apparatus 2 described herein, it is possible to generate a main scan image having excellent quality. Because the other advantageous effects are the same as those of the embodiment, the explanations thereof will be omitted.

A First Application Example

In the present application example, the supporting and moving mechanism 35 is moved in accordance with displacement of the center of gravity of the patient P on the supporting and moving mechanism 35. More specifically, the standing CT apparatus 1 described herein is configured to detect the center of gravity of the patient P supported by the supporting and moving mechanism 35 so that, on the basis of a detected displacement amount of the center of gravity, the moving of the supporting and moving mechanism 35 is controlled so as to compensate the displacement amount.

The supporting and moving mechanism 35 further includes a detecting unit configured to detect the center of gravity of the patient P supported by the supporting and moving mechanism 35. For example, the detecting unit is realized by using a center-of-gravity sensor. The center-of-gravity sensor is realized with, for example, a pressure sensor and a processor. The pressure sensor is configured to detect pressure on the tabletop applied from the soles of the patient and pressure on the tabletop or the block applied from a wheelchair or the like supporting the patient P. On the basis of an output from the pressure sensor, the processor is configured to calculate the center of gravity of the patient P. Because the calculation of the center of gravity based on the output from the pressure sensor can be realized, as appropriate, by using any of existing techniques, the explanations thereof will be omitted. The detecting unit thus detects the center of gravity of the patient P supported by the supporting and moving mechanism 35. The detecting unit is configured to output the calculated position of the center of gravity to the console device 100. In other words, the detecting unit has a function of monitoring the position of the center of gravity of the patient P.

Possible configurations of the detecting unit are not limited to the above example. In place of the pressure sensor, it is also acceptable to use any of various types of sensors such as an ultrasound sensor or an optical camera. When one of the various types of sensors or an optical camera is used in place of the pressure sensor, the detecting unit is not provided for the supporting and moving mechanism 35, but, for example, a plurality of detecting units are installed on a wall surface of the gantry 11 at the opening 15, while being positioned at angles different from the angles that allow the detecting units to oppose one another around the rotation axis A1. For example, when optical cameras are used as the detecting units, the optical cameras are configured to monitor the position and the posture of the patient P. Possible installation locations of the optical cameras are not limited to the wall surface of the gantry 11 at the opening 15. For example, the optical cameras may be installed on the ceiling positioned straight above the opening 15.

When the detecting units are realized by using any of the various types of sensors or the optical cameras, the processor is configured to calculate a tilt of the patient on the basis of data output from the sensors or the optical cameras and to further calculate the center of gravity on the basis of the calculated tilt. Because the calculation of the center of gravity based on the outputs from the sensors or the optical cameras can be realized, as appropriate, by using any of existing techniques, the explanations thereof will be omitted. Further, the detecting unit may be realized by the image processing function 117 included in the processing circuitry 107. In that situation, for example, the image processing function 117 is configured to detect the tilt of the patient P, on the basis of a plurality of pre-scan images PSI taken along the Z-direction. Subsequently, the image processing function 117 is configured to detect the center of gravity of the patient P on the basis of the detected tilt.

By employing the mechanism controlling function 119, on the basis of displacement amount of the center of gravity of the patient P, the processing circuitry 107 is configured to control the moving of the supporting and moving mechanism 35 so as to compensate the displacement amount. For example, on the basis of positions of the center of gravity observed in a time series, the mechanism controlling function 119 calculates displacement amounts of the center of gravity and displacement directions of the center of gravity of the patient P monitored by the detecting unit. While using the opposite directions of the displacement directions as moving directions, the mechanism controlling function 119 moves the tabletop by operating the driving mechanism on the basis of the moving directions and the displacement amounts.

Figure 12:
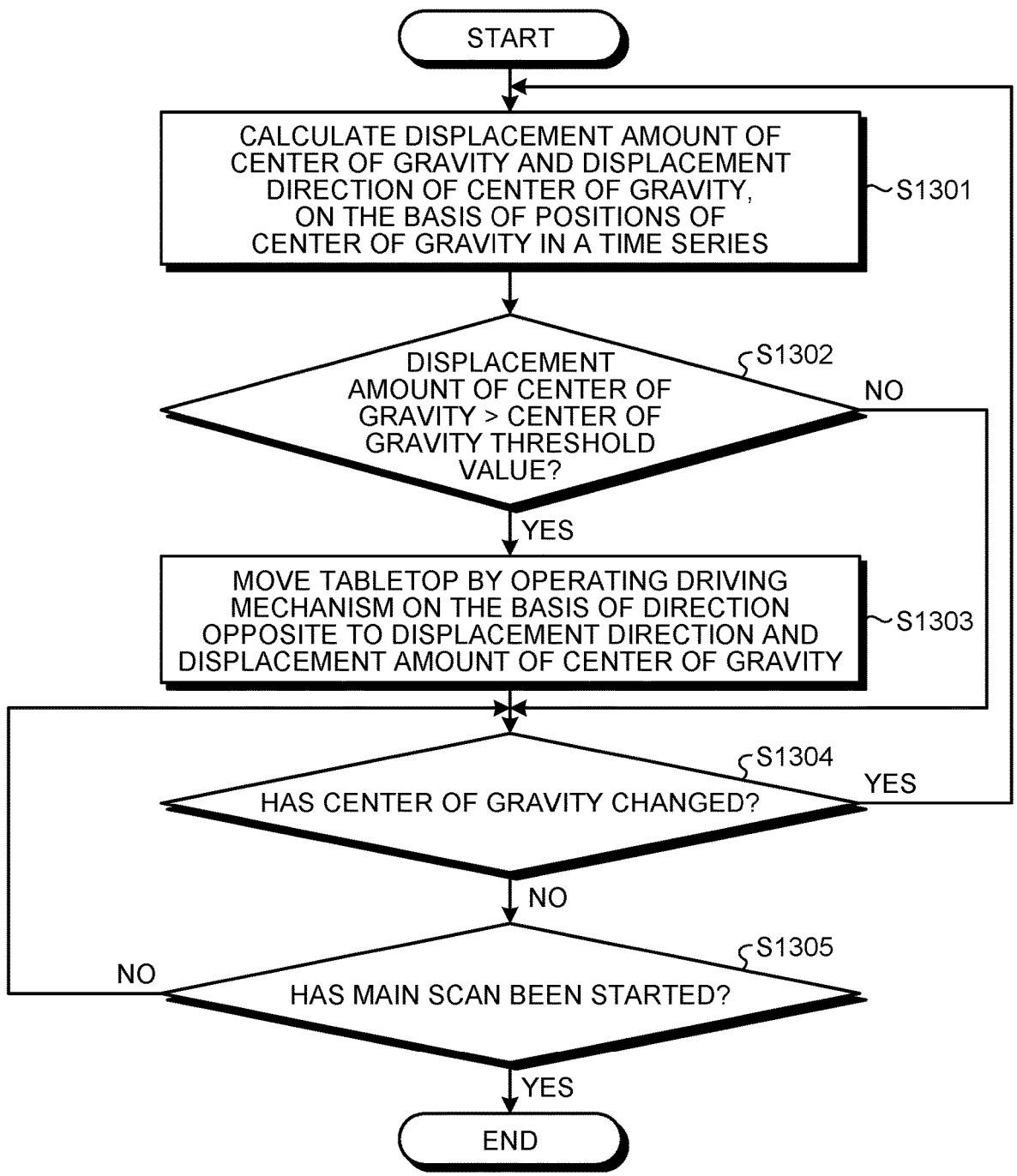
FIG. 12 is a flowchart illustrating an example of a procedure in a center-of-gravity following process according to a first application example of the embodiment.

Next, a process (hereinafter, "center-of-gravity following process") to move the supporting and moving mechanism 35 so as to follow the changes in the center of gravity of the patient P on the supporting and moving mechanism 35 will be explained. FIG. 12 is a flowchart illustrating an example of a procedure in the center-of-gravity following process. For example, it is possible to perform, as appropriate, the center-of-gravity following process at any point in time before a main scan is performed.

The Center-of-Gravity Following Process

Figure 13:
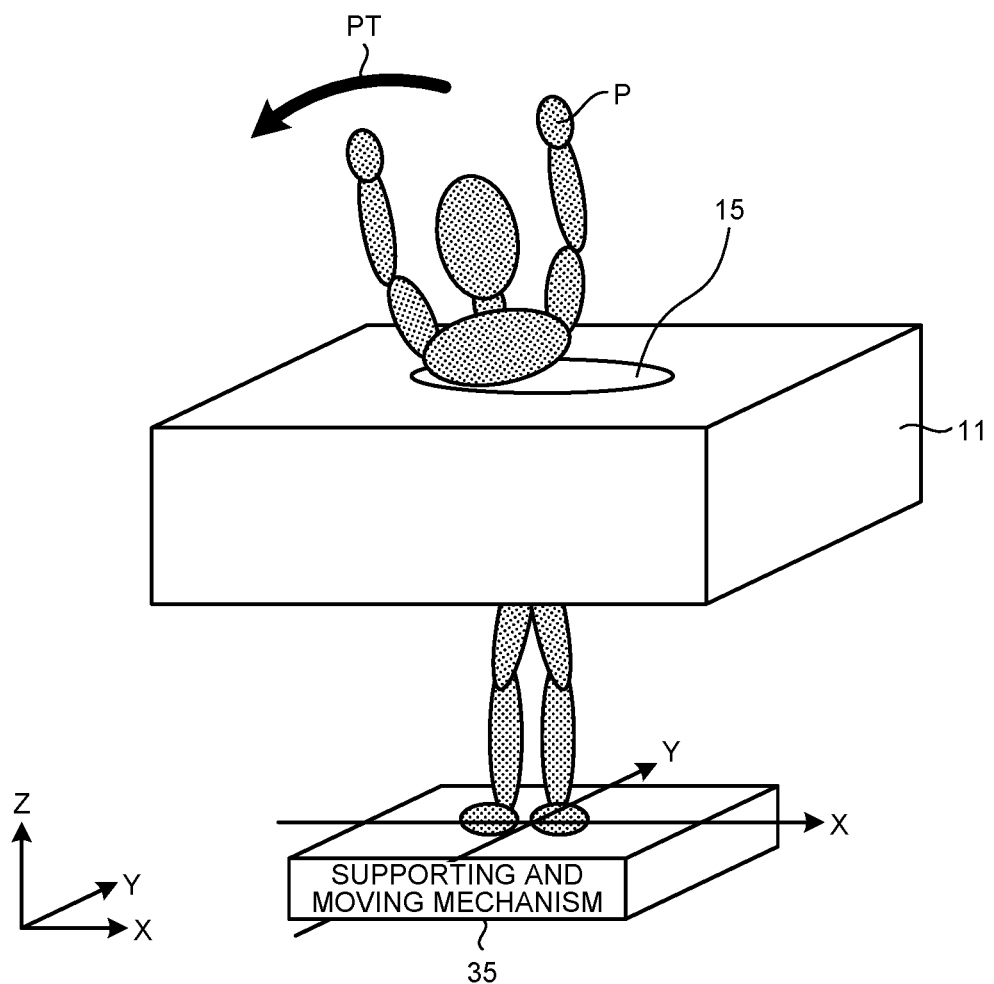
FIG. 13 is a drawing according to the first application example of the embodiment illustrating an example in which the center of gravity has changed due to a tilt of the patient.

Step S1301:

By employing the mechanism controlling function 119, the processing circuitry 107 calculates a change in the center of gravity (a displacement amount of the center of gravity) and the displacement direction of the center of gravity, on the basis of positions of the center of gravity of the patient P detected by the detecting unit. FIG. 13 is a drawing illustrating an example in which the center of gravity has changed due to a tilt PT of the patient P. As illustrated in FIG. 13, when the center of gravity of the patient P has moved due to the tilt PT of the posture of the patient P, the mechanism controlling function 119 calculates the displacement amount of the center of gravity and the displacement direction of the center of gravity corresponding to the moving of the center of gravity.

Step S1302:

When the displacement amount of the center of gravity exceeds a predetermined threshold value (hereinafter, "center of gravity threshold value") (step S1302: Yes), the process at step S1303 will be performed. On the contrary, when the displacement amount of the center of gravity is smaller than the center of gravity threshold value (step S1302: No), the process at step S1304 will be performed. The center of gravity threshold value is set in advance and stored in the memory 101.

Figure 14:
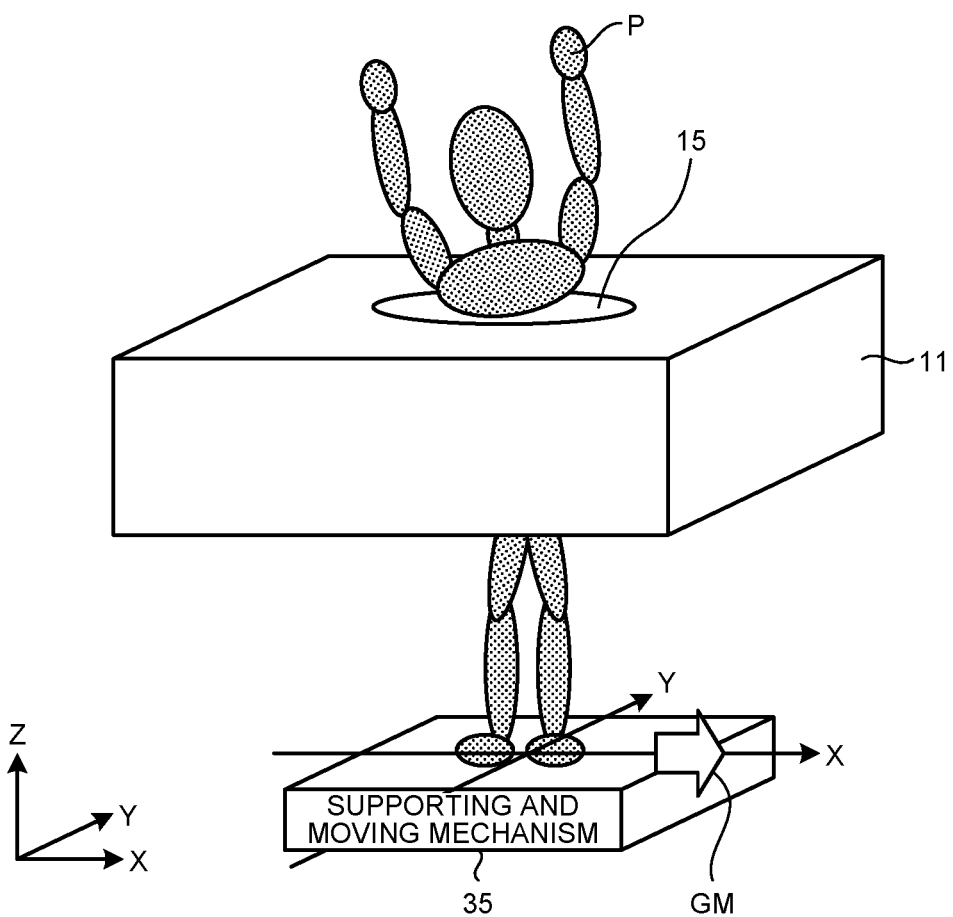
FIG. 14 is a drawing according to the first application example of the embodiment illustrating an example in which the supporting and moving mechanism is moved in an X direction in conjunction with the moving of the center of gravity of the patient due to the tilt of the posture of the patient.

Step S1303:

By employing the mechanism controlling function 119, the processing circuitry 107 controls the supporting and moving mechanism 35 on the basis of the moving direction, which is the opposite direction of the displacement direction of the center of gravity, and the displacement amount of the center of gravity. Under the control of the mechanism controlling function 119, the supporting and moving mechanism 35 moves, by employing the driving mechanism, the tabletop by the displacement amount of the center of gravity in the moving direction. FIG. 14 is a drawing illustrating an example in which the supporting and moving mechanism 35 is moved in the X direction by a moving amount GM, in conjunction with the moving of the center of gravity of the patient P due to the tilt PT of the posture of the patient P. As illustrated in FIG. 14, even when the center of gravity has changed due to the tilt PT of the posture of the patient P or the like, the supporting and moving mechanism 35 moves so as to compensate the moving of the center of gravity.

Further, the processing circuitry 107 may cause the display device 103 or a monitor provided on the gantry 11 or the like to display the displacement amount of the center of gravity and the displacement direction of the center of gravity corresponding to the moving of the center of gravity. In that situation, the mechanism controlling function 119 may manually move the supporting and moving mechanism 35 according to an instruction from the operator provided via the input interface 105.

Step S1304:

When a change has occurred to the center of gravity of the patient P on the basis of the outputs from the detecting unit (step S1304: Yes), the processes at step S1301 and thereafter will be performed. On the contrary, when no change has occurred to the center of gravity of the patient P on the basis of the outputs from the detecting unit (step S1304: No), the process at step S1305 will be performed.

Step S1305:

When a main scan is performed according to an instruction from the user provided via the input interface 105 (step S1305: Yes), the center-of-gravity following process ends. On the contrary, when the main scan is not performed (step S1305: No), the process at step S1304 is repeatedly performed.

When the standing CT apparatus 1 according to the first application example described above is used, the center of the gravity of the patient P supported by the supporting and moving mechanism 35 is detected so that, on the basis of the detected displacement amount of the center of gravity, the moving of the supporting and moving mechanism 35 is controlled so as to compensate the displacement amount. With this arrangement, by using the standing CT apparatus 1 described herein, it is possible to move the supporting and moving mechanism 35 so as to compensate the change in the center of gravity even when the center of gravity has changed due to the tilt PT of the posture of the patient P or the like. Consequently, by using the standing CT apparatus 1 described herein, it is possible to compensate the displacement of the center of gravity even when the center of gravity has changed. It is therefore possible to perform the main scan in the position desired by the user. Consequently, by using the standing CT apparatus 1 described herein, it is possible to generate a main scan image having excellent quality. Because the other advantageous effects are the same as those of the embodiment, the explanations thereof will be omitted.

A Second Application Example

In the present application example, the injection of the gas into the plurality of gas bags 37 and the ejection of the gas from the plurality of gas bags 37 described in the modification example are controlled in accordance with displacement of the center of gravity of the patient P on the supporting and moving mechanism 35. In other words, on the basis of the displacement of the center of gravity of the patient P, the mechanism controlling function 119 is configured to control the pumps 39 so as to compensate the displacement. The configuration in the present application example is the same as that illustrated in FIG. 7. In the sections below, some of the processes in the center-of-gravity following process according to the present application example that are different from those in the first application example will be explained.

Step S1303:

By employing the mechanism controlling function 119, the processing circuitry 107 determines a gas injection amount or a gas ejection amount with respect to each of the plurality of gas bags 37 on the basis of a correspondence table (hereinafter, "center of gravity displacement correspondence table") related to displacement directions of the center of gravity, displacement amounts of the center of gravity, and displacement of the center of gravity. For example, the center of gravity displacement correspondence table is a correspondence table indicating, with regard to each of the plurality of gas bags 37, a correspondence relationship among gas injection amounts and gas ejection amounts with respect to displacement directions of the center of gravity, displacement amounts of the center of gravity, and weights and heights of the patient P. The center of gravity displacement correspondence table is stored in the memory 101, in advance.

By employing the mechanism controlling function 119, the processing circuitry 107 is configured to control each of the plurality of pumps 39, according to the gas injection amount or the gas ejection amount determined with respect to each of the plurality of gas bags 37. The mechanism controlling function 119 controls the pumps 39 until the bag internal pressure levels detected by the pressure sensors provided for the gas bags 37 reach the pressure threshold value. For example, while the gas is injected into any one of the gas bags 37, when the bag internal pressure has reached the pressure threshold value, the mechanism controlling function 119 controls the pump 39 connected to the gas bag 37 so as to stop the injection of the gas. Because the other control procedures over the pumps 39 are similar to those in the modification example, the explanations thereof will be omitted.

When the standing CT apparatus 2 according to the second application example described above is used, the center of gravity of the patient P supported by the supporting and moving mechanism 35 is detected so that, on the basis of the detected displacement amounts of the center of gravity, the operations of the pumps 39 are controlled so as to compensate the displacement amounts. Because the advantageous effects of the present application example are the same as those of the first application example, the explanations thereof will be omitted.

A Third Application Example

Figure 15:
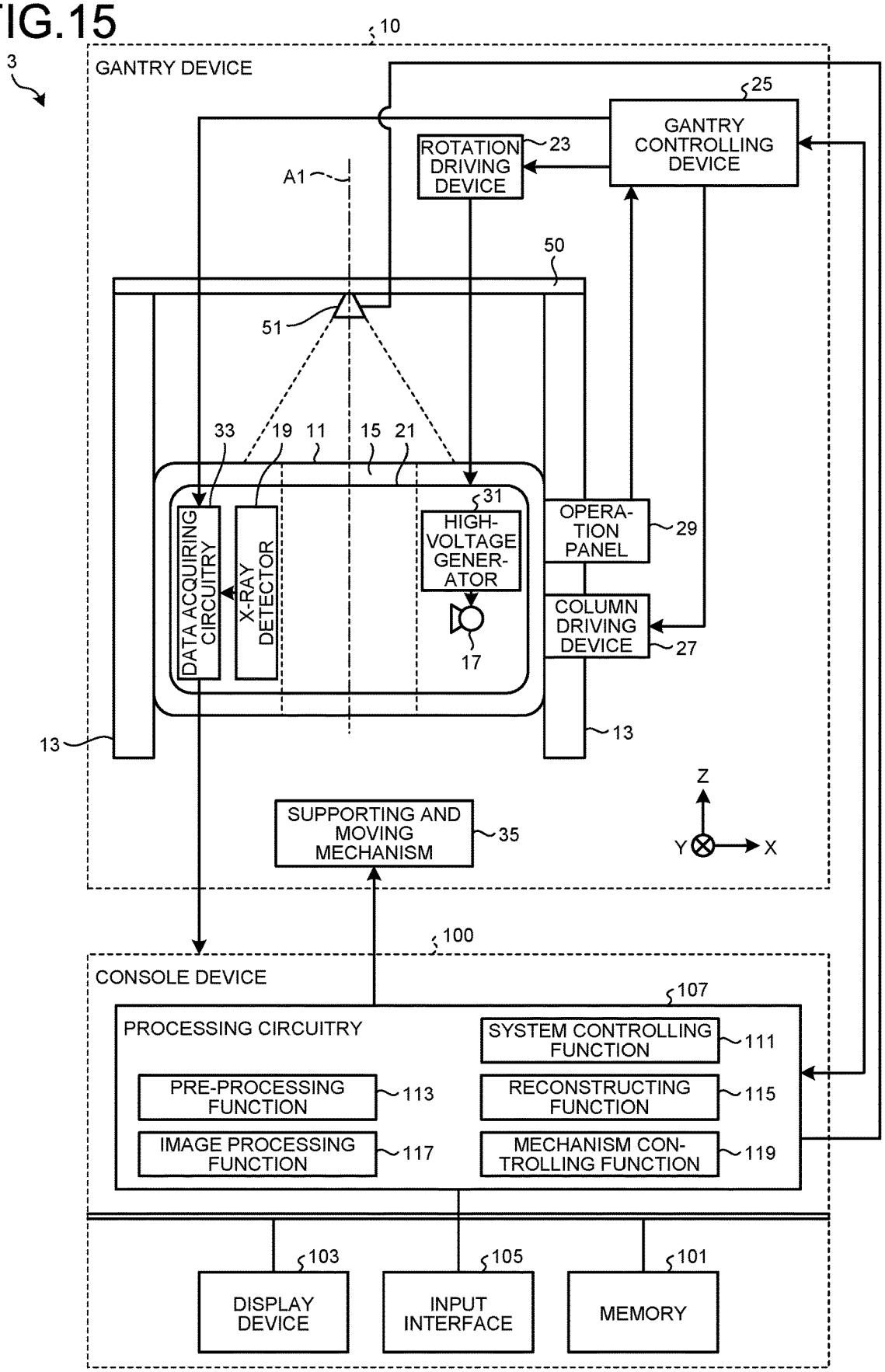
FIG. 15 is a diagram illustrating an exemplary configuration of a standing CT apparatus according to a third application example of the embodiment.

In the present application example, the supporting and moving mechanism 35 is moved without using the displacement of the center of gravity of the patient P. FIG. 15 is a diagram illustrating an exemplary configuration of a standing CT apparatus 3 according to the present application example. In the following sections, the differences in FIG. 15 from FIG. 1 will be explained. A beam 50 extends horizontally from the upper end of at least one of the columns 13. For example, the beam 50 is spanned between the upper ends of the pair of columns 13. In other words, the beam 50 is disposed so as to bridge across the pair of columns 13. When a single column 13 is used, the beam 50 is cantilevered by the upper end of the one column 13. For example, the beam 50 supports a camera (e.g., an optical camera) 51 in a position straight above the rotation axis A1. In other words, the optical camera 51 is arranged on the beam 50 extending horizontally from the upper end of at least one column 13 and is capable of imaging the patient P positioned at the opening 15 of the gantry 11. In a modification example of the present application example, the optical camera 51 may be, for example, provided on the ceiling of the examination room in which the standing CT apparatus 3 is installed. In that situation, the beam 50 is omitted.

The optical camera 51 is provided on one of: the beam 50 extending horizontally from the upper end of at least one column 13; and the ceiling of the examination room in which the standing CT apparatus 3 is installed. The angle of view of the optical camera 51 includes the opening (bore) 15. With this arrangement, the optical camera 51 is capable of imaging the patient P positioned at the opening 15 of the gantry 11. The optical camera 51 is configured to image the patient P at predetermined time intervals (with a predetermined framerate). As a result, the optical camera 51 outputs a plurality of images of the patient P (hereinafter, "patient images") in a time series, to the processing circuitry 107.

By employing the image processing function 117, the processing circuitry 107 is configured to recognize the position of the patient P (e.g., the head of the patient P) within the patient images. Because it is possible to apply an existing technique such as a trained model that is trained in advance or a segmentation process, for example, to the recognition of the position of the patient P (hereinafter, "patient position") in the patient images, the explanations thereof will be omitted. On the basis of the plurality of patient positions in the time series, the image processing function 117 is configured to determine shift amounts of the patient P. For example, the image processing function 117 determines a shift amount of the patient P with respect to each of predetermined time intervals, by calculating the difference between a patient position (hereinafter, "reference position") at the time of taking a scanogram image and a patient position obtained after the scanogram image was taken. Alternatively, the image processing function 117 may determine a shift amount of the patient P with respect to each of predetermined time intervals, by calculating the difference between any two patient positions that are chronologically next to each other. Further, on the basis of the differences, the image processing function 117 determines shift directions of the patient P.

Figure 16:
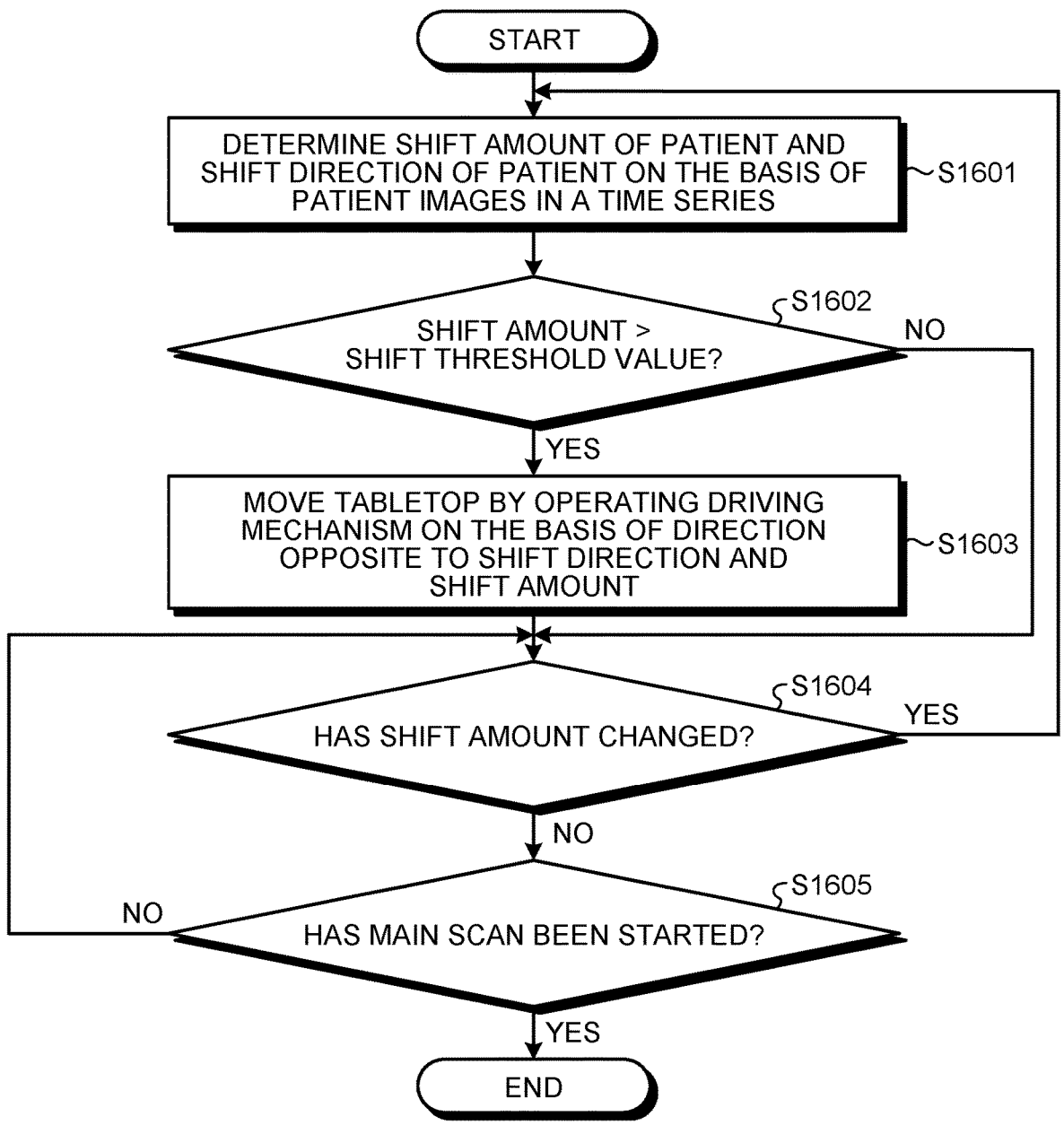
FIG. 16 is a flowchart illustrating an example of a procedure in a shift following process according to the third application example of the embodiment.

By employing the mechanism controlling function 119, on the basis of the shift amounts of the patient P in the images obtained by the optical camera 51, the processing circuitry 107 is configured to control the moving of the supporting and moving mechanism 35 so as to compensate the shift amounts. In the sections below, a process (hereinafter, "shift following process") to move the supporting and moving mechanism 35 so as to follow changes in the shifting of the patient P on the supporting and moving mechanism 35 will be explained. FIG. 16 is a flowchart illustrating an example of a procedure in the shift following process. For example, it is possible to perform, as appropriate, the shift following process at any point in time before a main scan is performed.

The Shift Following Process

Step S1601:

When the patient images are obtained by the optical camera 51, the processing circuitry 107 determines a shift amount of the patient P and the shift direction of the patient P on the basis of the patient images in the time series, by employing the image processing function 117.

Step S1602:

By employing the mechanism controlling function 119, the processing circuitry 107 compares the shift amount with a predetermined threshold value (hereinafter, "shift threshold value"). The shift threshold value is set in advance and stored in the memory 101. When the shift amount exceeds the shift threshold value (step S1602: Yes), the process at step S1603 will be performed. When the shift amount is smaller than the shift threshold value (step S1602: No), the process at step S1604 will be performed.

Step S1603:

By employing the mechanism controlling function 119, the processing circuitry 107 controls the supporting and moving mechanism 35, on the basis of a moving direction, which is the opposite direction of the shift direction, and the shift amount. More specifically, the mechanism controlling function 119 reads, from the memory 101, a table keeping shift amounts in correspondence with moving amounts of the supporting and moving mechanism 35. After that, the mechanism controlling function 119 determines the moving amount by referring to the read table to find a match for the determined shift amount. Under the control of the mechanism controlling function 119, the supporting and moving mechanism 35 moves the tabletop in the moving direction by the moving amount, by employing the driving mechanism. In this manner, the mechanism controlling function 119 controls the moving of the supporting and moving mechanism 35 so as to compensate the shift amount.

Further, the processing circuitry 107 may cause the display device 103 or a monitor provided on the gantry 11 or the like to display the shift amount and the moving direction. In this situation, the mechanism controlling function 119 may manually move the supporting and moving mechanism 35 in accordance with the shift amount, according to an instruction from the operator provided via the input interface 105.

Step S1604:

When a change has occurred to the shift amount of the patient P (step S1604: Yes), the processes at step S1601 and thereafter will be performed by employing the image processing function 117. When no change has occurred to the shift amount of the patient P (step S1604: No), the process at step S1605 will be performed by employing the image processing function 117.

Step S1605:

When a main scan is performed according to an instruction from the user provided via the input interface 105 (step S1605: Yes), the shift following process ends. When the main scan is not performed (step S1605: No), the process at step S1604 is repeatedly performed.

When the standing CT apparatus 3 according to the third application example described above is used, the optical camera 51 capable of imaging the patient P positioned at the opening 15 of the gantry 11 is provided on one of: the beam 50 extending horizontally from the upper end of at least one of the columns 13 or the ceiling of the examination room in which the standing CT apparatus 3 is installed so that, on the basis of the shift amounts of the patient P in the images obtained by the optical camera 51, the moving of the supporting and moving mechanism 35 is controlled so as to compensate the shift amounts. Consequently, by using the standing CT apparatus 3 described herein, even when the patient P shifts, it is possible to move the supporting and moving mechanism 35 so as to compensate the shifting of the patient P in a real-time manner, without the need to calculate the center of gravity of the patient P. As a result, by using the standing CT apparatus 3 described herein, it is possible to compensate the shifting of the patient P with the real-time feedback even when the patient P shifts. Accordingly, it is possible to perform the main scan in the position desired by the user. Because the other advantageous effects are the same as those in the embodiment, the explanations thereof will be omitted.

A Fourth Application Example

In the present application example, the supporting and moving mechanism 35 is moved without using the displacement of the center of gravity of the patient P. More specifically, in the present application example, a load distribution of the patient P supported by the supporting and moving mechanism 35 is detected so that, on the basis of a change amount in the load distribution, the moving of the supporting and moving mechanism 35 is controlled so as to compensate the change amount. In the following sections, differences between the first application example and the present application example will be explained.

Figure 17:
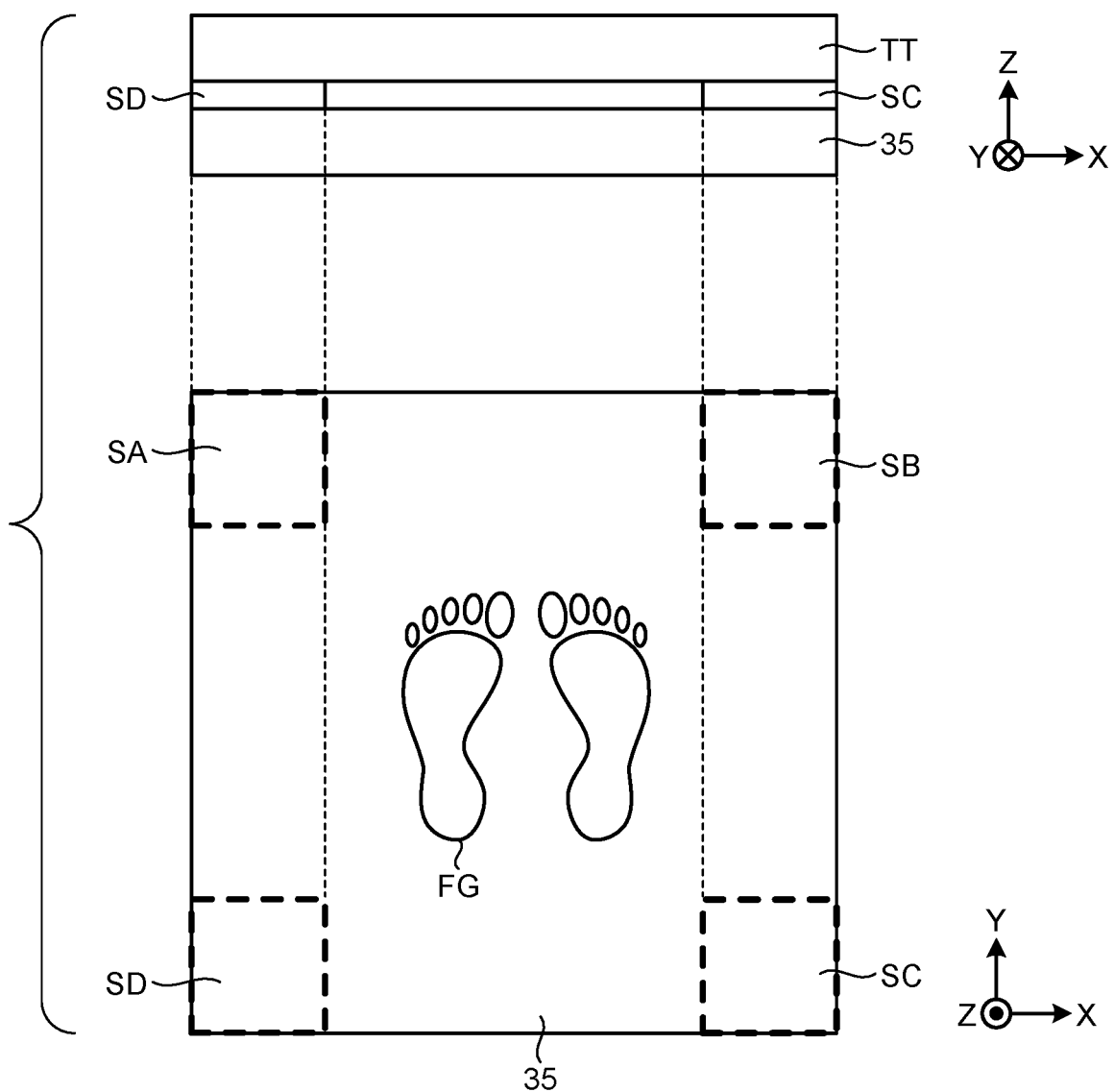
FIG. 17 is a drawing according to a fourth application example of the embodiment illustrating an example of a plurality of sensors provided between the supporting and moving mechanism and a tabletop.

FIG. 17 is a drawing according to the present application example illustrating an example of a plurality of sensors (SA, SB, SC, and SD) provided between the supporting and moving mechanism 35 and a tabletop TT. The tabletop TT is provided with footprint figures FG. The patient P stands on the tabletop TT while fitting his/her feet to the footprint figures FG. The plurality of sensors illustrated in FIG. 17 correspond to detecting units. In this situation, possible relative positional relationships among the plurality of sensors, the supporting and moving mechanism 35, and the tabletop TT are not limited to the example illustrated in FIG. 17. Further, for example, the detecting units may be realized by using a plurality of sensors of which the quantity is equal to "n×m" (where n and m are each a natural number of 2 or larger). In that situation, the plurality of sensors of which the quantity is equal to "n×m" are two-dimensionally arranged, for example, along the X direction and the Y direction while being positioned between the supporting and moving mechanism 35 and the tabletop TT.

The plurality of sensors realizing the detecting units are realized by using, for example, pressure sensors or load sensors. In the following sections, to explain a specific example, the plurality of sensors are assumed to be load sensors. The load sensor SA is configured to output a detected load Wa to the processing circuitry 107. The load sensor SB is configured to output a detected load Wb to the processing circuitry 107. The load sensor SC is configured to output a detected load Wc to the processing circuitry 107. The load sensor SD is configured to output a detected load Wd to the processing circuitry 107.

By employing the mechanism controlling function 119, the processing circuitry 107 is configured to measure a load distribution of the patient P on the tabletop TT at predetermined time intervals, on the basis of the plurality of loads (Wa, Wb, Wc, and Wd) output from the plurality of load sensors (SA, SB, SC, and SD). For example, the load distribution corresponds to a distribution of a plurality of load measured values corresponding to a relative positional relationship among the plurality of load sensors with respect to the tabletop TT. On the basis of a plurality of load distributions in a time series, the mechanism controlling function 119 is configured to determine shifting of the patient P. For example, the image processing function 117 determines shifting of the patient P with respect to each of predetermined time intervals, by calculating the difference between a load distribution (hereinafter, "reference load distribution") at the time of taking a scanogram image and a load distribution obtained after the scanogram image was taken. Alternatively, the image processing function 117 may determine shifting of the patient P with respect to each of predetermined time intervals, by calculating the difference between any two load distributions that are chronologically next to each other.

More specifically, the mechanism controlling function 119 compares the calculated differences with a predetermined threshold value (hereinafter, "distribution threshold value"). The distribution threshold value is set in advance and stored in the memory 101. When any of the differences exceeds the distribution threshold value, the mechanism controlling function 119 determines that the patient shifted. In this situation, on the basis of the most recent load distribution, the mechanism controlling function 119 determines a moving amount of the supporting and moving mechanism 35. For example, when the plurality of load sensors are installed as indicated in FIG. 17, the mechanism controlling function 119 determines a shift amount in the +Y direction as a value expressed as (Wa+Wb)/2−(Wc+Wd)/2 and determines a shift amount in the +X direction as a value expressed as (Wb+Wc)/2−(Wd+Wa)/2.

When the plurality of load sensors are two-dimensionally arranged (in the formation of n×m load sensors) on the bottom side of the tabletop TT, the mechanism controlling function 119 is able to detect the positions of the left and the right feet of the patient P, by calculating an in-plane peak of the loads on the tabletop TT. By tracking the positions of the left and the right feet, the mechanism controlling function 119 is able to determine positional shifting of the patient, i.e., a moving amount of the patient P.

When the standing CT apparatus 1 according to the fourth application example described above is used, the load distributions of the patient P supported by the supporting and moving mechanism 35 are detected so that, on the basis of change amounts in the detected load distributions, the moving of the supporting and moving mechanism 35 is controlled so as to compensate the change amounts. Consequently, by using the standing CT apparatus 1 described herein, even when the patient P shifts, it is possible to move the supporting and moving mechanism 35 so as to compensate the shifting of the patient P in a real-time manner, without the need to calculate the center of gravity of the patient P. Because the other advantageous effects are the same as those in the embodiment, the explanations thereof will be omitted.

A Fifth Application Example

In the present application example, a grip part that can be gripped by the patient P positioned at the opening 15 of the gantry 11 is provided while being fixed to one of: a beam extending horizontally from the upper end of at least one of the columns 13; the ceiling of the examination room in which the standing CT apparatus 1 is installed; and the bottom face of the examination room. For example, the grip part includes a rod-shaped bar that can be gripped by the patient P.

For example, when the grip part is fixed to the beam or the ceiling, the grip part may be formed to have a substantially L-shape, for example. In this situation, the grip part includes: a first section extending vertically downward while a first end of the L-shaped grip part is fixed to the beam or the ceiling; and a horizontal second section extending parallel to the ground (or the floor surface) from the second end of the first section. In another example, when the grip part is fixed to the beam or the ceiling, the grip part may include two bars and another bar. A first end of each of the two bars is fixed to the beam or the ceiling, while the two bars each extend vertically downward. The other bar is fixed to the vicinity of the second end of each of the two bars while extending parallel to the ground (or the floor surface). In yet another example, when the grip part is fixed to the bottom face of the examination room, the grip part is realized with a bar extending vertically upward, inside the opening, from either the floor surface or the supporting and moving mechanism 35.

When the standing CT apparatus 1 according to the fifth application example described above is used, the patient P positioned at the opening 15 of the gantry 11 is able to grip the grip part (the bar) fixed to one of: the beam 50 extending horizontally from the upper end of at least one of the columns 13; the ceiling of the examination room in which the standing CT apparatus 1 is installed; and the bottom face of the examination room. Consequently, according to the present application example, it is possible to enhance stability of the patient P at the time of moving the patient P in relation to the positional alignment of the ROI with the imaging center. Further, by using the standing CT apparatus 1 described herein, it is possible to prevent the situation where the CT image from the main scan becomes blurry due to the upper body of the patient P being unstable.

A Sixth Application Example

In the present application example, the grip part in the fifth application example is fixed to either the beam or the ceiling of the examination room via a moving frame that is horizontally movable, so that the mechanism controlling function 119 controls moving of the moving frame. In the following sections, to explain a specific example, let us assume that the grip part is L-shaped and is installed on the beam via the moving frame.

Figure 18:
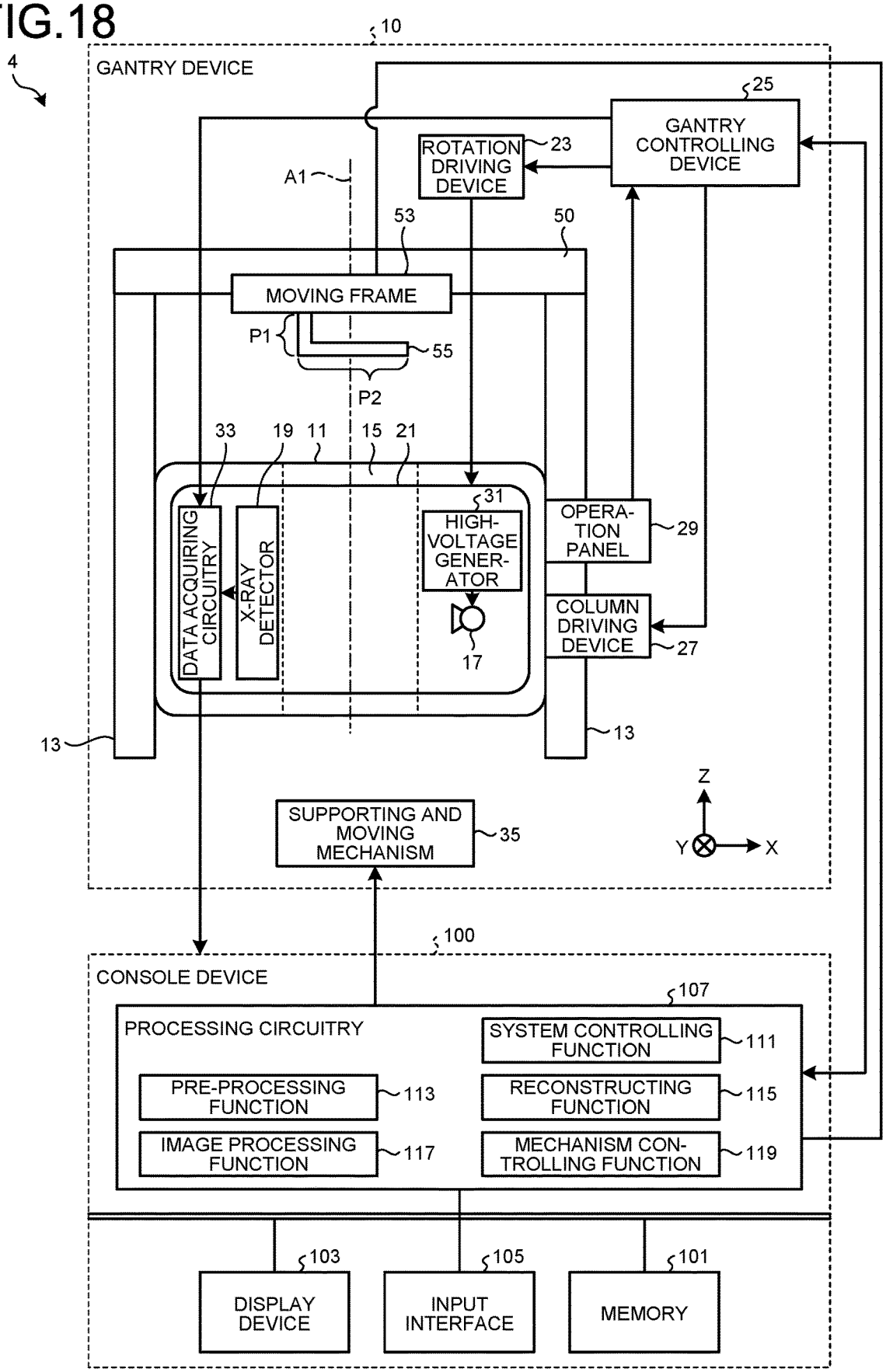
FIG. 18 is a diagram illustrating an exemplary configuration of a standing CT apparatus according to a sixth application example of the embodiment.

FIG. 18 is a diagram illustrating an exemplary configuration of a standing CT apparatus 4 according to the present application example. As illustrated in FIG. 18, a moving frame 53 is fixed to the beam 50. The moving frame 53 supports a grip part 55 so as to be movable in the horizontal directions (the X and Y directions). Under the control of the mechanism controlling function 119, the moving frame moves the grip part 55 horizontally. The moving frame 53 includes a moving mechanism configured to move the grip part 55 in at least one of the X-axis direction and the Y-axis direction, i.e., along a horizontal direction.

For example, the moving mechanism includes: at least one guide (e.g., a linear guide such as a linear motion guide) having a block that supports the grip part 55 and a rail that guides the block; and a driving mechanism configured to move the block of the guide along the rail. The driving mechanism includes, for example, any of various types of motors to generate a driving force and any of various types of transmission mechanisms to transmit the driving force to the block. According to a control signal output from the mechanism controlling function 119, the moving frame 53 is configured to generate the driving force by employing the driving mechanism. By using the generated driving force, the moving frame 53 is configured to move the grip part along the horizontal direction.

Next, a position aligning process according to the present application example will be explained. FIG. 19 is a flowchart illustrating an example of a procedure in the position aligning process according to the present application example. Because steps S1901 and S1902 in FIG. 19 correspond to and are the same as steps S201 and S202 in FIG. 2, the explanations thereof will be omitted.
The Position Aligning Process
Step S1903:

By employing the mechanism controlling function 119, the processing circuitry 107 outputs a moving amount and a moving direction of the moving frame 53, on the basis of the center position of the ROI and the position of the imaging center. Further, the mechanism controlling function 119 may cause a monitor provided on the gantry 11 or at least one of the columns 13 or the display device 103 to display the moving amount and the moving direction of the moving frame 53, together with the center position of the ROI and the position of the imaging center. With this arrangement, it is possible to inform the user of the moving amount and the moving direction of the moving frame 53. In another example, the mechanism controlling function 119 may cause the display device 103 to display the moving amount and the moving direction of the moving frame 53, together with the pre-scan image PSI. In that situation, the user may, as appropriate, revise the moving amount and the moving direction of the moving frame 53, via the input interface 105.

Step S1904:

By employing the mechanism controlling function 119, the processing circuitry 107 moves the moving frame 53, by operating the driving mechanism on the basis of the moving direction and the moving amount. In that situation, according to an instruction from the operator provided via the input interface 105, the mechanism controlling function 119 may manually move the moving frame, in accordance with a moving amount and a moving direction being input or revised by the user.

When the standing CT apparatus 4 according to the sixth application example described above is used, the grip part 55 is fixed, via the moving frame 53, to one of: the beam 50 extending horizontally from the upper end of at least one of the columns 13; and the ceiling of the examination room in which the standing CT apparatus 4 is installed, so as to control the moving of the moving frame 53. Because the advantageous effects of the present application example are the same as the advantageous effects of the embodiment and the advantageous effects of the fifth application example, the explanations thereof will be omitted. In a modification example of the present application example, only the grip part 55 may be movable, while the tabletop TT is not movable. In that situation, the supporting and moving mechanism 35 may be omitted, in which case, the user may prompt the patient P to move.

A Seventh Application Example

In the present application example, it is judged whether or not the tabletop is to be moved to a position (hereinafter, "contact position") corresponding to contact between a part of the patient P and the gantry 11, on the basis of a moving amount and a moving direction calculated from the center position of the ROI and the position of the imaging center CI, for example, so as to correct the moving amount according to a result of the judgment. For example, the contact position corresponds to the position of the supporting and moving mechanism 35 observed while the part of the patient P is in contact with the gantry 11.

The mechanism controlling function 119 is configured to judge whether or not the tabletop is to be moved to the contact position, on the basis of the moving amount and the moving direction calculated from the center position of the ROI and the position of the imaging center CI. When it is determined that the tabletop is to be moved to the contact position, the mechanism controlling function 119 is configured to decrease (correct) the moving amount so as to prevent the tabletop from being moved to the contact position. The mechanism controlling function 119 is configured to control the supporting and moving mechanism 35 in accordance with the corrected moving amount. In other words, the mechanism controlling function 119 is configured to control the moving of the supporting and moving mechanism 35 so as to prevent the contact between the part of the patient P and the gantry 11.

When the standing CT apparatus 1 according to the seventh application example described above is used, it is judged whether or not the supporting and moving mechanism 35 is to move to the contact position, on the basis of the region of interest (ROI) in the pre-scan image PSI and the imaging center CI of the imaging system. When it is determined that the supporting and moving mechanism 35 is to move to the contact position, the moving amount of the supporting and moving mechanism 35 is corrected so as to prevent the contact between the part of the patient P and the gantry 11, so that the supporting and moving mechanism 35 is controlled in accordance with the corrected moving amount. With this arrangement, by using the standing CT apparatus 1 according to the present application example, it is possible to arrange the ROI in the vicinity of the imaging center CI, while preventing the contact between the part of the patient P and the gantry 11. It is therefore possible to improve throughput of the examination of the patient P.

An Eighth Application Example

In the present application example, it is judged whether or not a partial region of the patient P is to escape from a Field Of View (FOV) of the imaging system due to the moving of the supporting and moving mechanism 35, on the basis of the moving amount and the moving direction calculated from the center position of the ROI and the position of the imaging center CI, for example. When it is determined that the partial region is to escape from the field of view, the display device 103 displays an area escaping from the field of view. Subsequently, in the present application example, the moving amount of the supporting and moving mechanism 35 is changed according to an instruction from the user being input in accordance with the escaping area, so that the supporting and moving mechanism 35 is controlled in accordance with the changed moving amount.

The mechanism controlling function 119 is configured to judge whether or not the partial region of the patient P is to escape from the field of view of the imaging system due to the moving of the supporting and moving mechanism 35, on the basis of the moving amount and the moving direction calculated from the center position of the ROI and the position of the imaging center CI. When it is determined that the partial region is to escape from the field of view, the mechanism controlling function 119 causes the display device 103 to display the area (hereinafter, "out-of-FOV area") escaping from the field of view, by using the pre-scan image PSI. As a result, the out-of-FOV area is visually recognized by the user. The mechanism controlling function 119 is configured to change the moving amount of the supporting and moving mechanism 35 according to an instruction from the user provided via the input interface 105. The mechanism controlling function 119 is configured to control the supporting and moving mechanism 35 in accordance with the changed moving amount.

When the standing CT apparatus 1 according to the eighth application example described above is used, it is judged whether or not the partial region of the patient P is to escape from the field of view due to the moving of the supporting and moving mechanism 35, on the basis of the region of interest (ROI) in the pre-scan image PSI and the imaging center CI of the imaging system. When it is determined that the partial region is to escape from the field of view, the display device 103 displays the out-of-FOV area, so that the moving amount of the supporting and moving mechanism 35 is changed according to the instruction from the user being input in accordance with the out-of-FOV area and so that the supporting and moving mechanism 35 is controlled in accordance with the changed moving amount. With this arrangement, when the standing CT apparatus 1 according to the present application example is used, because the display device 103 displays the out-of-FOV area when it is determined that the partial region is to escape from the field of view, it is possible to visually inform the user of the out-of-FOV area. As a result, by using the standing CT apparatus 1 according to the present application example, it is possible to control the supporting and moving mechanism 35 in accordance with the moving amount changed by the user. Consequently, when the standing CT apparatus 1 according to the present application example is used, because it is possible to change the moving amount according to the instruction from the user corresponding to the out-of-FOV area, it is possible to perform a main scan on the ROI conforming to the intension of the user. Because the other advantageous effects of the present application example are the same as those of the embodiments, the explanations thereof will be omitted.

A Ninth Application Example

In the present application example, it is judged whether or not a partial region of the patient P is to escape from the field of view due to the moving of the supporting and moving mechanism 35, on the basis of the moving amount and the moving direction calculated from the center position of the ROI and the position of the imaging center CI, for example. When it is determined that the partial region is to escape from the field of view, the moving amount of the supporting and moving mechanism 35 is changed so as to prevent the partial region from escaping from the field of view, so that the supporting and moving mechanism 35 is controlled in accordance with the changed moving amount.

The mechanism controlling function 119 is configured to judge whether or not the partial region of the patient P is to escape from the field of view of the imaging system due to the moving of the supporting and moving mechanism 35, on the basis of the moving amount and the moving direction calculated from the center position of the ROI and the position of the imaging center CI. When it is determined that the partial region is to escape from the field of view, the mechanism controlling function 119 is configured to change the moving amount of the supporting and moving mechanism 35 so as to prevent the partial region from escaping from the field of view. More specifically, the mechanism controlling function 119 changes (decreases) the moving amount so as to prevent the partial region from escaping from the field of view. The mechanism controlling function 119 is configured to control the supporting and moving mechanism 35 in accordance with the changed moving amount.

When the standing CT apparatus 1 according to the ninth application example described above is used, it is judged whether or not the partial region of the patient P is to escape from the field of view due to the moving of the supporting and moving mechanism 35, on the basis of the region of interest (ROI) in the pre-scan image PSI and the imaging center CI of the imaging system. When it is determined that the partial region is to escape from the field of view, the moving amount of the supporting and moving mechanism 35 is changed so as to prevent the partial region from escaping from the field of view, so that the supporting and moving mechanism 35 is controlled in accordance with the changed moving amount. With this arrangement, by using the standing CT apparatus 1 according to the present application example, it is possible to arrange the ROI in the vicinity of the imaging center CI, while preventing the partial region of the patient P from escaping from the field of view. It is therefore possible to improve throughput of the examination of the patient P.

A Tenth Application Example

In the present application example, one of the eighth and the ninth application examples is implemented in accordance with a scan plan of a main scan to be performed on the patient P. The scan plan includes, for example, the number of scans, a range of the scans, radiation exposure timing, a radiation exposure condition, and an image processing condition.

The mechanism controlling function 119 is configured to judge whether or not a partial region of the patient P is to escape from the field of view of the imaging system due to the moving of the supporting and moving mechanism 35, on the basis of the moving amount and the moving direction calculated from the center position of the ROI and the position of the imaging center CI. When it is determined that the partial region is to escape from the field of view, the mechanism controlling function 119 is configured to perform one of the following in accordance with the scan plan of the main scan related to the patient P: causing the display device 103 to display the out-of-FOV area; and changing the moving amount of the supporting and moving mechanism 35 so as to prevent the partial region from escaping from the field of view. When the out-of-FOV area is displayed on the display device 103, the mechanism controlling function 119 is configured to change the moving amount of the supporting and moving mechanism 35 according to an instruction from the user being input in accordance with the out-of-FOV area. The mechanism controlling function 119 is configured to control the supporting and moving mechanism 35 in accordance with the changed moving amount. Because the other advantageous effects of the present application example are the same as those of the eighth and the ninth application examples, the explanations thereof will be omitted.

When technical concepts of the embodiment are realized as a controlling method, the controlling method includes: employing the imaging system included in the gantry 11 supported so as to be movable in the vertical directions by at least one column 13 and imaging the patient P supported from underneath by the supporting and moving mechanism 35 installed so as to be movable in a direction intersecting the moving directions of the gantry 11; generating the image on the basis of the outputs from the imaging system; and controlling the moving of the supporting and moving mechanism 35. Because the procedure and advantageous effects of the position aligning process implemented by the controlling method are the same as those of the embodiment, the explanations thereof will be omitted.

According to at least one aspect of the embodiments, the plurality of application examples, and the modification examples described above, it is possible to obtain medical images having excellent quality.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

In relation to the above embodiments, the following notes are presented as certain aspects and optional characteristics of the present disclosure:

Note 1:
 A medical image diagnosis apparatus that including:
 at least one column configured to support a gantry related to imaging a patient so as to be movable in a vertical direction;
 a supporting and moving mechanism configured to support the patient from underneath, while being installed so as to be movable in a direction intersecting the moving direction of the gantry; and
 a mechanism controlling unit configured to control the moving of the supporting and moving mechanism.

Note 2:
 The gantry may include an imaging system related to the imaging of the patient.

Note 3:
 It is acceptable to further provide an image generating unit configured to generate an image on the basis of an output from the imaging system.

Note 4:
 The mechanism controlling unit may control the moving of the supporting and moving mechanism, on the basis of a region of interest in the image and an imaging center of the imaging system.

Note 5:
 The mechanism controlling unit may control the moving of the supporting and moving mechanism so as to align a center position of the region of interest with a position of the imaging center.

Note 6:
 The mechanism controlling unit may control the moving of the supporting and moving mechanism, according to an instruction from a user based on a region of interest in the image and an imaging center of the imaging system.

Note 7:
 The mechanism controlling unit may control the moving of the supporting and moving mechanism, according to an instruction from the user to align a center position of the region of interest with a position of the imaging center.

Note 8:
 It is acceptable to further provide a detecting unit configured to detect a center of gravity of the patient supported by the supporting and moving mechanism so that, on the basis of a displacement amount of the center of gravity, the mechanism controlling unit may control the moving of the supporting and moving mechanism so as to compensate the displacement amount.

Note 9:
 It is acceptable to further provide a camera which is positioned above an opening of the gantry and of which a field of view includes the inside of the opening of the gantry, while, on the basis of a shift amount of the patient within an image obtained by the camera, the mechanism controlling unit may control the moving of the supporting and moving mechanism so as to compensate the shift amount.

Note 10:
 The camera may be an optical camera capable of imaging the patient positioned at the opening of the gantry, while being disposed on one of: a beam extending horizontally from an upper end of the column; and a ceiling of an examination room in which the medical image diagnosis apparatus is installed.

Note 11:
 It is acceptable to further provide a detecting unit configured to detect a load distribution of the patient supported by the supporting and moving mechanism so that, on the basis of a change amount in the load distribution, the mechanism controlling unit may control the moving of the supporting and moving mechanism so as to compensate the change amount.

Note 12:
 The gantry may have an opening forming an imaging space related to the imaging, whereas the medical image diagnosis apparatus may further include: a plurality of gas bags configured to maintain a posture of the patient when being inflated by injection of gas, while being provided on a wall surface of the gantry at the opening; and a plurality of pumps configured to inject the gas into the gas bags and to eject the gas from the gas bags, and the mechanism controlling unit may further control the injection of the gas and the ejection of the gas by the pumps, in conjunction with the control over the moving.

Note 13:
 It is acceptable to further provide a detecting unit configured to detect a center of gravity of the patient supported by the supporting and moving mechanism so that, on the basis of displacement of the center of gravity, the mechanism controlling unit may control the pumps so as to compensate the displacement.

Note 14:
 It is acceptable to further provide a grip part that can be gripped by the patient positioned at an opening of the gantry.

Note 15:
 The grip part may be fixed to one of: a beam extending horizontally from an upper end of the column; a ceiling of an examination room in which the medical image diagnosis apparatus is installed; and a bottom face of the examination room.

Note 16:
 The grip part may be fixed to one of the beam and the ceiling via a moving frame that is horizontally movable, and the mechanism controlling unit may control moving of the moving frame.

Note 17:
 On the basis of a region of interest in the image and an imaging center of the imaging system, the mechanism controlling unit may judge whether or not the supporting and moving mechanism is to move to a position corresponding to contact between a part of the patient and the gantry. When it is determined that the supporting and moving mechanism is to move to the position corresponding to the contact, the mechanism controlling unit may correct a moving amount of the supporting and moving mechanism so as to prevent the contact between the part of the patient and the gantry, and may control the supporting and moving mechanism in accordance with the corrected moving amount.

Note 18:
 On the basis of a region of interest in the image and an imaging center of the imaging system, the mechanism controlling unit may judge whether or not a partial region of the patient is to escape from a field of view of the imaging system due to the moving of the supporting and moving mechanism. When it is determined that the partial region is to escape from the field of view, the mechanism controlling unit may cause a display device to display an area escaping from the field of view, may change a moving amount of the supporting and moving mechanism according to an instruction from a user being input in accordance with the escaping area, and may control the supporting and moving mechanism in accordance with the changed moving amount.

Note 19:

On the basis of a region of interest in the image and an imaging center of the imaging system, the mechanism controlling unit may judge whether or not a partial region of the patient is to escape from a field of view of the imaging system due to the moving of the supporting and moving mechanism. When it is determined that the partial region is to escape from the field of view, the mechanism controlling unit may change a moving amount of the supporting and moving mechanism, so as to prevent the partial region from escaping from the field of view, and may control the supporting and moving mechanism in accordance with the changed moving amount.

Note 20:

On the basis of a region of interest in the image and an imaging center of the imaging system, the mechanism controlling unit may judge whether or not a partial region of the patient is to escape from a field of view of the imaging system due to the moving of the supporting and moving mechanism. When it is determined that the partial region is to escape from the field of view, the mechanism controlling unit may perform one of the following in accordance with a scan plan related to the patient: causing a display device to display an area escaping from the field of view; and changing a moving amount of the supporting and moving mechanism so as to prevent the partial region from escaping from the field of view. When the escaping area is displayed on the display device, the mechanism controlling unit may change the moving amount of the supporting and moving mechanism according to an instruction from a user being input in accordance with the escaping area, and may control the supporting and moving mechanism in accordance with the changed moving amount.

Note 21:

The medical image diagnosis apparatus may be configured to image the patient in a standing state.

Note 22:

The medical image diagnosis apparatus may be one of: an X-ray computed tomography apparatus and a positron emission tomography apparatus.

Note 23:

The gantry may implement scanogram imaging on the patient, so that the region of interest may be specified in the image generated by the scanogram imaging.

Note 24:

A controlling method including: employing an imaging system included in a gantry supported by at least one column so as to be movable in a vertical direction and imaging a patient supported, from underneath, by a supporting and moving mechanism installed so as to be movable in a direction intersecting the moving direction of the gantry; generating an image on the basis of an output from the imaging system; and controlling the moving of the supporting and moving mechanism.

Note 25:

A medical image diagnosis apparatus that includes: a gantry including an imaging system related to imaging a patient; at least one column configured to support the gantry so as to be movable in a vertical direction; an image generating unit configured to generate an image on the basis of an output from the imaging system; a supporting and moving mechanism configured to support the patient from underneath, while being installed so as to be movable in a direction intersecting the moving direction of the gantry; and an output unit configured to output information corresponding to one or both of a moving direction and a moving amount of the supporting and moving mechanism, on the basis of a region of interest of the patient and an imaging center of the imaging system.

What is claimed is:

1. A medical image diagnosis apparatus, comprising:
    a gantry including an imaging system related to imaging a patient;
    at least one column configured to support the gantry so as to be movable in a vertical direction;
    processing circuitry configured to generate an image based on an output from the imaging system; and
    a supporting and moving mechanism configured to support the patient from underneath, while being installed so as to be movable in a direction intersecting the moving direction of the gantry, wherein the processing circuitry is configured to control the moving of the supporting and moving mechanism,
    wherein the processing circuitry controls the moving of the supporting and moving mechanism, based on a region of interest in the image and an imaging center of the imaging system.

2. The medical image diagnosis apparatus according to claim 1, wherein the processing circuitry is further configured to control the moving of the supporting and moving mechanism so as to align a center position of the region of interest with a position of the imaging center.

3. The medical image diagnosis apparatus according to claim 1, further comprising:
    a sensor configured to detect a center of gravity of the patient supported by the supporting and moving mechanism,
    wherein based on a displacement amount of the center of gravity, the processing circuitry is further configured to control the moving of the supporting and moving mechanism so as to compensate the displacement amount.

4. The medical image diagnosis apparatus according to claim 1, further comprising a sensor configured to detect a load distribution of the patient supported by the supporting and moving mechanism, wherein
    based on a change amount in the load distribution, the processing circuitry is further configured to control the moving of the supporting and moving mechanism so as to compensate for the change amount.

5. The medical image diagnosis apparatus according to claim 1, wherein
    the gantry has an opening forming an imaging space related to the imaging,
    the medical image diagnosis apparatus further comprises
        a plurality of gas bags configured to maintain a posture of the patient when being inflated by injection of gas, while being provided on a wall surface of the gantry at the opening; and
        a plurality of pumps configured to inject the gas into the gas bags and to eject the gas from the gas bags, and
    the processing circuitry is further configured to control the injection of the gas and the ejection of the gas by the pumps, in conjunction with the control over the moving.

6. The medical image diagnosis apparatus according to claim 5, further comprising a sensor configured to detect a center of gravity of the patient supported by the supporting and moving mechanism, wherein based on a displacement of the center of gravity, the processing circuitry is further configured to control the pumps so as to compensate for the displacement.

7. The medical image diagnosis apparatus according to claim 1, wherein
based on a region of interest in the image and an imaging center of the imaging system, the processing circuitry is further configured to determine whether or not the supporting and moving mechanism is to move to a position corresponding to contact between a part of the patient and the gantry,
when determining that the supporting and moving mechanism is to move to the position corresponding to the contact, the processing circuitry is further configured to correct a moving amount of the supporting and moving mechanism so as to prevent the contact between the part of the patient and the gantry, and
the processing circuitry is further configured to control the supporting and moving mechanism in accordance with the corrected moving amount.

8. The medical image diagnosis apparatus according to claim 1, wherein
based on a region of interest in the image and an imaging center of the imaging system, the processing circuitry is further configured to determine whether or not a partial region of the patient is to escape from a field of view of the imaging system due to the moving of the supporting and moving mechanism,
when determining that the partial region is to escape from the field of view, the processing circuitry is further configured to cause a display device to display an area escaping from the field of view,
the processing circuitry is further configured to change a moving amount of the supporting and moving mechanism according to an instruction from a user being input in accordance with the escaping area, and
the processing circuitry is further configured to control the supporting and moving mechanism in accordance with the changed moving amount.

9. The medical image diagnosis apparatus according to claim 1, wherein
based on a region of interest in the image and an imaging center of the imaging system, the processing circuitry is further configured to determine whether or not a partial region of the patient is to escape from a field of view of the imaging system due to the moving of the supporting and moving mechanism,
when determining that the partial region is to escape from the field of view, the processing circuitry is further configured to change a moving amount of the supporting and moving mechanism, so as to prevent the partial region from escaping from the field of view, and
the processing circuitry is further configured to control the supporting and moving mechanism in accordance with the changed moving amount.

10. The medical image diagnosis apparatus according to claim 1, wherein
based on a region of interest in the image and an imaging center of the imaging system, the processing circuitry is further configured to determine whether or not a partial region of the patient is to escape from a field of view of the imaging system due to the moving of the supporting and moving mechanism,
when determining that the partial region is to escape from the field of view, the processing circuitry is further configured to perform one of the following in accordance with a scan plan related to the patient: causing a display device to display an area escaping from the field of view and changing a moving amount of the supporting and moving mechanism so as to prevent the partial region from escaping from the field of view,
when the escaping area is displayed on the display device, the processing circuitry is further configured to change the moving amount of the supporting and moving mechanism according to an instruction from a user being input in accordance with the escaping area, and
the processing circuitry is further configured to control the supporting and moving mechanism in accordance with the changed moving amount.

11. A medical image diagnosis apparatus, comprising:
a gantry including an imaging system related to imaging a patient;
at least one column configured to support the gantry so as to be movable in a vertical direction;
processing circuitry configured to generate an image based on an output from the imaging system; and
a supporting and moving mechanism configured to support the patient from underneath, while being installed so as to be movable in a direction intersecting the moving direction of the gantry, wherein the processing circuitry is configured to control the moving of the supporting and moving mechanism,
wherein the processing circuitry is further configured to control the moving of the supporting and moving mechanism, according to an instruction from a user based on a region of interest in the image and an imaging center of the imaging system.

12. The medical image diagnosis apparatus according to claim 11, wherein the processing circuitry is further configured to control the moving of the supporting and moving mechanism, according to an instruction from the user to align a center position of the region of interest with a position of the imaging center.

13. A medical image diagnosis apparatus, comprising:
a gantry including an imaging system related to imaging a patient;
at least one column configured to support the gantry so as to be movable in a vertical direction;
processing circuitry configured to generate an image based on an output from the imaging system; and
a supporting and moving mechanism configured to support the patient from underneath, while being installed so as to be movable in a direction intersecting the moving direction of the gantry, wherein the processing circuitry is configured to control the moving of the supporting and moving mechanism,
wherein the apparatus further comprises an optical camera configured to image the patient positioned at an opening of the gantry, while being disposed on one of a beam extending horizontally from an upper end of the column, and a ceiling of an examination room in which the medical image diagnosis apparatus is installed, and
based on a shift amount of the patient within an image obtained by the optical camera, the processing circuitry is further configured to control the moving of the supporting and moving mechanism so as to compensate the shift amount.

14. A medical image diagnosis apparatus, comprising:
a gantry including an imaging system related to imaging a patient;
at least one column configured to support the gantry so as to be movable in a vertical direction;
processing circuitry configured to generate an image based on an output from the imaging system; and a supporting and moving mechanism configured to support the patient from underneath, while being installed so as to be movable in a direction intersecting the moving direction of the gantry, wherein the processing circuitry is configured to control the moving of the supporting and moving mechanism, wherein the apparatus further comprises a bar that can be gripped by the patient positioned at an opening of the gantry and that is fixed to one of a beam extending horizontally from an upper end of the column, a ceiling of an examination room in which the medical image diagnosis apparatus is installed, and a bottom face of the examination room.

15. The medical image diagnosis apparatus according to claim 14, wherein the bar is fixed to one of the beam and the ceiling via a moving frame that is horizontally movable, and the processing circuitry is further configured to control moving of the moving frame.

16. A controlling method, comprising:

employing an imaging system included in a gantry supported by at least one column so as to be movable in a vertical direction and imaging a patient supported, from underneath, by a supporting and moving mechanism installed so as to be movable in a direction intersecting the moving direction of the gantry;

generating an image based on an output from the imaging system; and controlling the moving of the supporting and moving mechanism, based on a region of interest in the image and an imaging center of the imaging system.

17. A medical image diagnosis apparatus, comprising:

a gantry including an imaging system related to imaging a patient;

at least one column configured to support the gantry so as to be movable in a vertical direction;

processing circuitry configured to generate an image based on an output from the imaging system; and a supporting and moving mechanism configured to support the patient from underneath, while being installed so as to be movable in a direction intersecting the moving direction of the gantry, wherein the processing circuitry is further configured to output information corresponding to one or both of a moving direction and a moving amount of the supporting and moving mechanism, based on a region of interest of the patient and an imaging center of the imaging system.

* * * * *